(12) United States Patent
Letourneau et al.

(10) Patent No.: US 8,350,043 B2
(45) Date of Patent: Jan. 8, 2013

(54) AZINONE AND DIAZINONE V3 INHIBITORS FOR DEPRESSION AND STRESS DISORDERS

(75) Inventors: Jeffrey John Letourneau, East Windsor, NJ (US); Koc-Kan Ho, West Windsor, NJ (US); Michael J. Ohlmeyer, Plainsboro, NJ (US); Patrick Jokiel, Princeton, NJ (US); Christopher Mark Riviello, Morrisville, PA (US)

(73) Assignee: Pharmacopeia, Inc., Princeton, NJ (US)

( * ) Notice: Subject to any disclaimer, the term of this patent is extended or adjusted under 35 U.S.C. 154(b) by 652 days.

(21) Appl. No.: 11/422,710

(22) Filed: Jun. 7, 2006

(65) Prior Publication Data

US 2007/0037822 A1   Feb. 15, 2007

Related U.S. Application Data

(60) Provisional application No. 60/688,306, filed on Jun. 7, 2005.

(51) Int. Cl.
| | |
|---|---|
| C07D 213/02 | (2006.01) |
| C07D 213/24 | (2006.01) |
| C07D 213/63 | (2006.01) |
| A61K 31/44 | (2006.01) |
| A61K 31/4412 | (2006.01) |
| A61P 25/22 | (2006.01) |
| A61P 25/24 | (2006.01) |

(52) U.S. Cl. ............... 546/261; 546/268.1; 514/350
(58) Field of Classification Search ............ 546/261, 546/268.1; 514/350
See application file for complete search history.

(56) References Cited

U.S. PATENT DOCUMENTS

| | | | |
|---|---|---|---|
| 5,521,179 | A | 5/1996 | Bernstein et al. |
| 6,664,255 | B1 | 12/2003 | South et al. |
| 6,908,919 | B2 | 6/2005 | South et al. |
| 2005/0043313 | A1 | 2/2005 | South et al. |

FOREIGN PATENT DOCUMENTS

| | | |
|---|---|---|
| EP | 0509769 | 11/1996 |
| WO | 9965874 | 12/1999 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Golub et al., Science, 286, 531-537, 1999.*
Dermer et al., Bio/Technology, 1994, 12:320.*
Treschan et al., Anesthesiology, 105, 599-612, 2006.*
Serradeil-Le Gal et al., "Nonpeptide vasopressin receptor antagonists: development of selective and orally active V1a, V2 and V1b receptor ligands", Progress in Brain Research, vol. 139, 2002, 197-210.
Parlow et al., "Design, Parallel Synthesis and Crystal Structures of Pyrazinone Antithrombotics as Selective Inhibitors of the Tissue Factor VIIa Complex", Journal of Medicinal Chemistry, 2003, 46(19), 4050-4062.
International Search Report for corresponding patent application PCT/US2006/022025.

* cited by examiner

*Primary Examiner* — Venkataraman Balasubramanian
(74) *Attorney, Agent, or Firm* — Susan L. Hess; Gerard M. Devlin

(57) ABSTRACT

Substituted pyridines, pyrimidines, pyrazines, pyridinones, pyrimidinones, pyrazinones and phenylacetamides useful in treating depression, stress and other disorders are disclosed. The compounds are of the formualae:

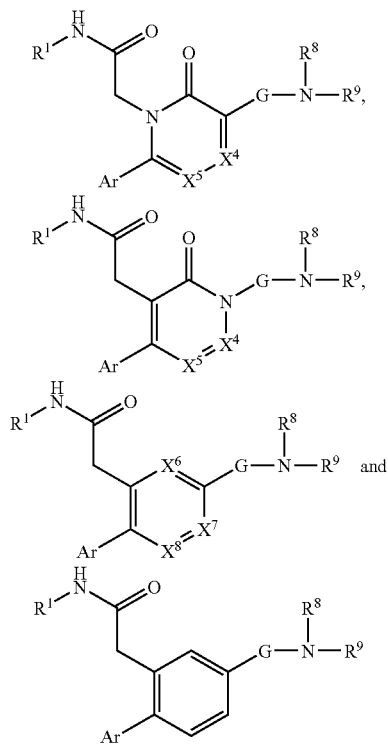

Other embodiments are also disclosed.

21 Claims, No Drawings

AZINONE AND DIAZINONE V3 INHIBITORS FOR DEPRESSION AND STRESS DISORDERS

CROSS-REFERENCE TO RELATED APPLICATIONS

This application claims priority from Provisional Patent Application Ser. No. 60/688,306, filed Jun. 7, 2005, the contents of which are incorporated herein by reference.

FIELD OF THE INVENTION

The invention relates to a chemical class of substituted pyridines, pyrimidines, pyrazines, pyridinones, pyrimidinones, pyrazinones and phenylacetamides useful in treating depression, stress and other disorders.

BACKGROUND OF THE INVENTION

The hypothalamo-pituitary-adrenal (HPA) axis is the major stress axis in humans and other mammals. A variety of stressors (and multiple other classes of stimuli) cause release of the hormone ACTH (adrenocorticotropic hormone) from the anterior pituitary gland. ACTH enters the systemic circulation and acts on the adrenal cortex to promote synthesis and release of glucocorticoid hormone (the major endogenous glucocorticoid being cortisol in humans and corticosterone in rodents). The glucocorticoids exert a broad spectrum of effects, the main purpose of which is to mobilize energy sources for successful responsiveness and eventual adaptation to the stressor.

Abnormally elevated HPA axis activity in man is associated with the development of a variety of psychiatric disturbances, some of which are stress-related in aetiology. Elevated cortisol levels, which are indicative of HPA axis hyperactivity and loss of normal negative feedback regulatory processes, are a common finding in affective disorders and various other psychiatric disturbances, and are widely utilized as a diagnostic tool (Holsboer et al., *Biol. Psych.* 1986, 21, 601-611). It is generally considered that dysregulation of the HPA axis is a reflection of enhanced vulnerability and poor adaptation to chronic stress and that chronic stress therefore plays a major role in the development of affective illness (Sperry and Carlson, DSM-IV diagnosis to treatment, $2^{nd}$ Edition, Taylor & Francis, 1996). This central concept is supported by experimental evidence utilizing animal models of chronic stress, where aberrant HPA function closely resembles that seen in clinical settings (De Goeij et al., *Neuroendocrinology,* 1991, 53, 150-159; Plotsky and Meaney, *Mol. Brain Res.* 1993, 18, 195-200).

The major secretagogues for ACTH in humans and rats are CRH (corticotropin releasing hormone) and AVP (arginine vasopressin). Within the HPA axis these peptide hormones are synthesized by the parvocellular neurones of the paraventricular nucleus (PVN) of the hypothalamus. The axons of these neurones project to the external zone of the median eminence, from where the hormone products enter the hypophysial portal system to bathe the corticotrope cells that manufacture ACTH. CRH and AVP act synergistically at the corticotrope to regulate ACTH secretion in both and in man.

The HPA axis is most potently activated by psychological stressors (i.e., those which require a cognitive assessment of the stimulus). The patterns of AVP and CRH release vary as a function of the type of stressor involved. Acute stress, whether physical or psychological, elicits rapid and robust CRH release. For several psychological stressors, however, chronic application elicits enhanced AVP storage in the median eminence, increased mRNA synthesis, and reduction in AVP neurosecretory granules, whereas similar markers of CRH synthesis and release are relatively unaffected. These findings, when considered together with clinical and experimental data indicating that stress enhances the number of PVN neurones co-expressing CRH and AVP, and that brain levels of AVP are elevated in patients suffering from affective disorders, show that AVP plays an important role as an ACTH secretagogue. Further, they show that chronic psychological stress is associated with a shift in emphasis from CRH to AVP-controlled HPA axis activity. Thus AVP plays a pivotal role in the genesis of the HPA hyperactivity documented in affective disorders.

The actions of AVP at the pituitary cortocotrope are mediated by the vasopressin V3 (or V1b) receptor, which is known and has been cloned (human receptor: Sugimoto et al., *J. Biol. Chem.,* 1994, 269, 27088-27092). A report of clinical studies in depressed patients in which blunted ACTH responses to CRH could be restored by concomitant administration of desmopressin (dDAVP, an AVP agonist with V3 affinity) confirms the involvement of the V3 receptor in depression (Scott and Dinan, *Life Sciences,* 1998, 62, 1985-1988). A study in rodents with non-selective peptide V3 antagonists indicates that the V3 receptor does play a functional role in control of pituitary ACTH release (Bernardini et al., *Neuroendocrinology,* 1994, 60, 503-508). Vasopressin antagonists are thus utilized to modulate and normalize pituitary ACTH release and subsequent HPA axis dysfunction in CNS disorders which are characterized by abnormal HPA axis negative feedback mechanisms.

Studies have indicated that V3 antagonists may be useful in the treatment of aggressive behavior [see Wersinger et al. *Mol. Psychiatry* 7, 975-984 (2002); Blanchard et al. *Pharmcol. Biochem. Behav.* 80, 189-194 (2005); and Wersinger et al. Horm. Behav. 46, 638-645 (2004)]; insomnia in elderly patients [see Kalamatianos et al. J. Neuroendocrinol. 16, 493-501 (2004)]; cancer [see Dahia el al. *J. Clin. Endocrim. Metab.* 81, 1768-1771 (1996)]; Cushing's Disease [see Perraudin et al. *J. Clin. Endocrin. Metab.* 80, 2661-2667 (1995)]; pancreatic disease [see Folny el al. *Am. J. Physiol.* 285, E566-576 (2003)]; and to effect diuresis [see Chen el al. *J. Neurosci. Res.* 60, 761-766 (2000)].

In addition to the V3 receptor, vasopressin also activates peripheral receptors, i.e., the V1a receptor, predominantly found on liver and vascular tissue and the V2 receptor, predominantly found on kidney tissue. Interaction at these receptors mediates the pressor and antidiuretic actions of AVP.

Whilst there are several non-peptide low-molecular weight antagonists known which are selective for the V1a or the V2 receptor (for a recent review see Freidinger and Pettibone, *Medicinal Research Reviews,* 1997, 17, 1-16), there are only a small number of non-peptide ligands known with selectivity for the V3 receptor (see for example, WO 01/55130 and WO 04/009585). There exists therefore a need for further non-peptide V3 selective antagonists which are both safe and effective.

SUMMARY OF THE INVENTION

There are provided, in accordance with an embodiment of the invention, compounds of formulae:

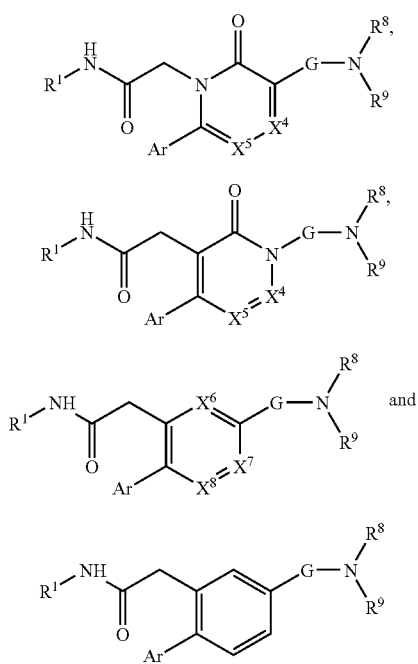

In genera I and II, $X^4$-$X^5$ is chosen from $CR^4$—$CR^5$, $N$—$CR^5$ and $CR^4$—$N$; in genus III, one of $X^6$, $X^7$ and $X^8$ is N and the other two are $CR^4$ and $CR^5$.

$R^1$ is chosen from $(C_{1-10})$alkyl, $(C_{3-10})$cycloalkyl, $[(C_{3-10})$cycloalkyl$(C_{1-2})$alkyl], said $(C_{1-10})$alkyl, $(C_{3-10})$cycloalkyl, and $[(C_{3-10})$cycloalkyl $(C_{1-2})$alkyl] being optionally substituted with one or more halogens, $(C_{1-6})$alkoxy, $(C_{2-6})$alkenyl, $(C_{2-6})$alkynyl, phenyl or benzyl;

Ar is chosen from
  (i) $(C_{6-10})$aryl, optionally substituted within 1-3 substituents selected from halogen, hydroxy, cyano, $COOR^5$, $NR^6R^7$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens;
  (ii) $(C_{5-10})$heteroaryl optionally substituted with a substituent selected from methyl, $(C_{1-6})$alkyloxy or halogen; and
  (iii) $(C_{4-7})$cycloalkyl;

$R^4$ and $R^5$ are independently chosen from H, $(C_{1-6})$alkyl, $(C_{1-6})$alkyloxy or halogen, said $(C_{1-6})$alkyl and $(C_{1-6})$alkyloxy being optionally substituted with one or more halogens, G is a linking moiety spanning 4 to 7 atoms between termini; and $R^8$ and $R^9$ are residues that, in combination, maintain the basicity of N.

When $X^4$-$X^5$ is $CR^4$—N and G is alkylene, $R^1$ must be chosen from $(C_{1-6})$alkyl, $(C_{3-6})$cycloalkyl and $[(C_{3-6})$cycloalkyl $(C_{1-2})$alkyl]. When $R^1$ is not restricted to this subset of values, G is a linking moiety incorporating at least one of (a) an sp2 hybridized carbon; or (b) a cyclic structure. Alternatively, when $R^8$ and $R^9$ together form a 4- to 7-membered nitrogenous heterocycle, G may additionally be —$N(R^{10})$—$(C_{4-6})$alkylene for all values of $R^1$, $R^{10}$ is H or $(C_{1-6})$alkyl.

A subgenus of compounds in accordance with embodiments of the invention is the genus I:

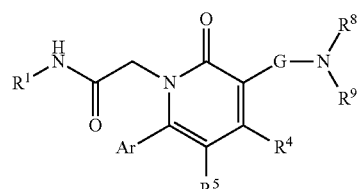

The genus I can be divided into three subgenera:

pyridinones:

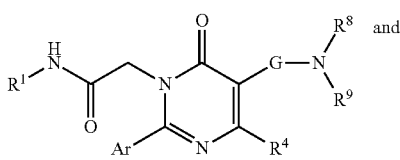

pyrimidinones:

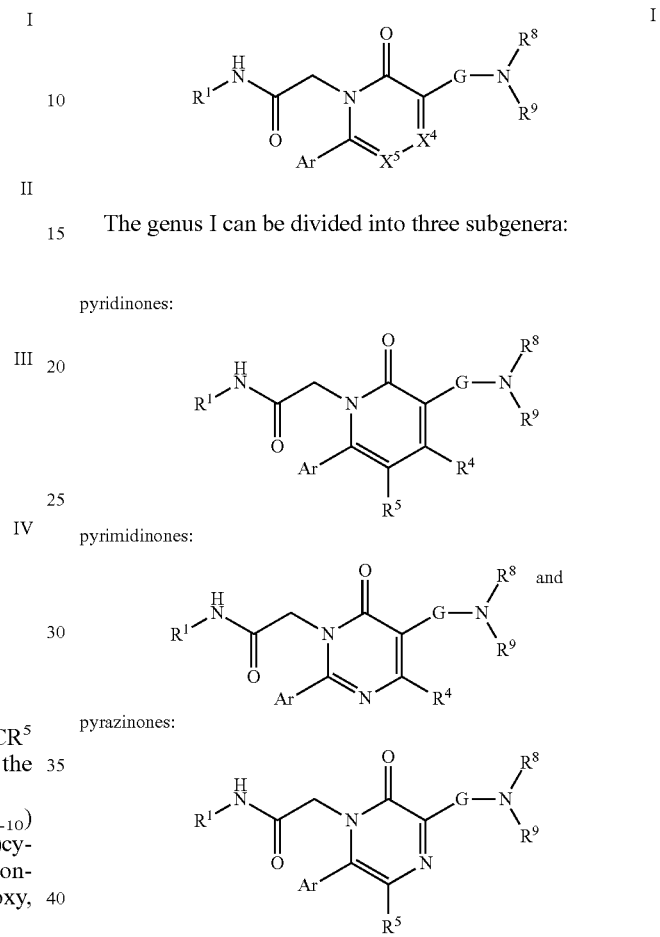

pyrazinones:

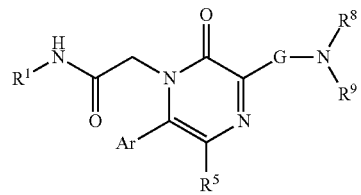

In another embodiment of the invention there are provided pharmaceutical formulations comprising a pharmaceutically acceptable carrier and a compound as described above.

In another embodiment of the invention there are provided methods for treating depression, stress disorders, aggressive behavior, insomnia in elderly patients, cancer, Cushing's Disease, and pancreatic disease and to effect diuresis using a compound as described above.

DETAILED DESCRIPTION OF THE INVENTION

In some embodiments of the invention, there are provided pyridines, pyrimidines, pyrazines, pyridinones, pyrimidinones, pyrazinones and phenylacetamides falling within a general formula

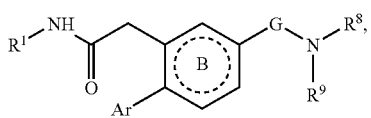

in which B represents a six-membered, planar carbocycle or planar nitrogen heterocycle.

As indicated above, G is a linking moiety spanning 4 to 7 atoms between termini. In other words, the —NR⁸R⁹ must be 4 to 7 atoms removed from the ring B. The precise constituents of G are not critical. Typically G will incorporate either an sp2 hybridized carbon or a cyclic structure. When R⁸ and R⁹ together form a 4 to 7-membered nitrogenous heterocycle, G may be —N(R¹⁰)—(C₄₋₆)alkylene. Thus, for example, G may be a (C₄-C₇)-alkylene in which one or more —CH₂— may be replaced by —S—, —S(O)—, —SO₂—, —O—, —C(=O)—, —CHOH—, —NH—, CHF, CF₂, —CH(O-loweralkyl)-, —CH(O-loweracyl)-, —CH(loweralkyl)- or —C(loweralkyl)₂-, with the provisos that (1) adjacent —CH₂— residues cannot be replaced by —S—, —S(O)—, —SO₂— or —O—; and (2) —S—, —S(O)—, —SO₂—, —O— and —NH— residues cannot be separated only by a single carbon. G may also be an optionally substituted carbocycle or heterocycle, attached to the B ring and to —NR⁸R⁹ by a direct bond or by a C₁-C₅ alkylene chain. G may also be an optionally substituted nitrogenous heterocycle, attached to the B ring by a direct bond or by a C₁-C₅ alkylene chain; in this case a nitrogen of the nitrogenous heterocycle may correspond to —NR⁸R⁹ so that R⁹ becomes formally part of G. R⁸ and R⁹ may also be taken together and attach to G so as to form a nitrogen-containing heterocycle, e.g. a pyridine ring attached at one of the ring carbon atoms to the linker which links the pyridine ring to ring B. In such cases, there will be 4 to 7 atoms between the ring B and the carbon atom of the nitrogen-containing heterocycle.

The residues R⁸ and R⁹ must maintain the basicity of N. For example, alkyl residues of various sorts are within the invention; alkylene and similar residues (e.g. alkylene with heteroatom interruption) that tie the nitrogen into a ring are within the invention. Even residues that introduce aromaticity are tolerated, as long as the nitrogen remains basic (e.g. pyridine). Acyl residues (e.g. R⁸=acetyl), which destroy the basicity of the nitrogen, are outside the invention. Under certain circumstances, one or both of R⁸ and R⁹ may be hydrogen. These concepts are explained more fully in the text and examples below.

A genus in accordance with some embodiments of the invention comprises pyridinones, pyrimidinones and pyrazinones that fall within the general formula I above.

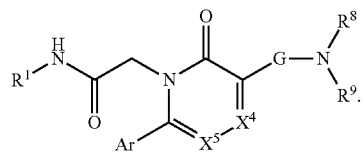

In these compounds, X⁴-X⁵ is CR⁴—CR⁵, N—CR⁵ or CR⁴—N.

Examples of subgenera in accordance with embodiments of the invention include the subgenus in which —NR⁸R⁹ is a saturated nitrogenous heterocycle of 3 to 10 carbons in one or two rings, preferably a piperidine or morpholine, and G is a (C₃₋₁₀)hydrocarbon chain attached to the pyridinone, pyrimidinone or pyrazinone through an amide or amine:

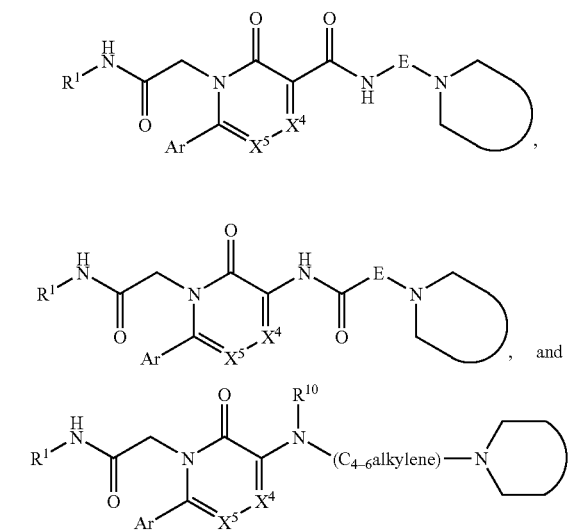

wherein E is (C₂₋₁₀)hydrocarbon; and

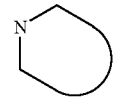

is a saturated nitrogenous heterocycle of 3 to 10 carbons in one or two rings. The nitrogenous heterocycle may be substituted, for example, 4-hydroxypiperidin-1-yl, 4-hydroxy-4-methylpiperidin-1-yl and 4,4-dimethylpiperidin-1-yl. The (C₂₋₁₀)hydrocarbon may be straight chain, branched or cyclic as long as the 4-7 atom spacing between —NR⁸R⁹ and the pyridinone, pyrimidinone or pyrazinone ring is maintained. Examples of species in this subgenus include:

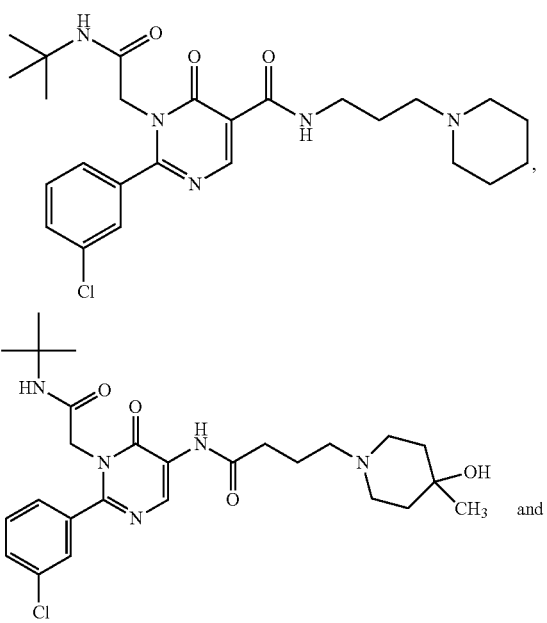

-continued

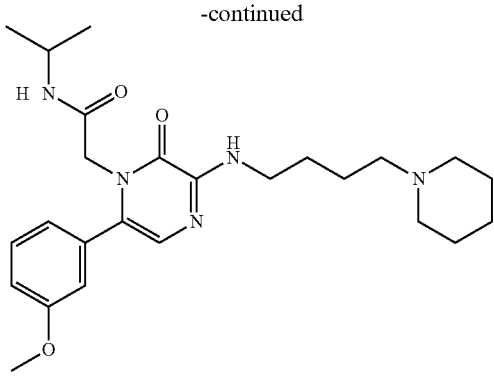

A further example of a subgenus in accordance with embodiments of the invention is the subgenus in which —NR$^8$R$^9$ is attached via a direct bond or (C$_{1-6}$)hydrocarbon, J, to a single ring carbocycle or heterocycle of 4 to 7 atoms or a two ring carbocycle or heterocycle of 9 to 13 atoms, (A).

The carbocycle or heterocycle (A)

is directly attached to the pyridinone, pyrimidinone or pyrazinone:

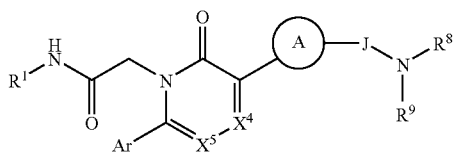

In some embodiments (A)

is a five or six-membered nitrogenous heterocycle (e.g. oxadiazolyl, pyrrolidinyl and piperidinyl) and J is methylene, ethylene or propylene, and in some embodiments —NR$^8$R$^9$ is chosen from piperidine, morpholine and —N[C$_{1-3}$alkyl]$_2$. Examples of species in this subgenus include:

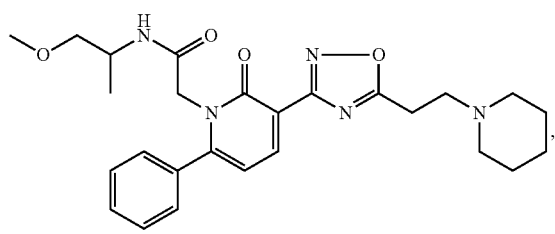

-continued

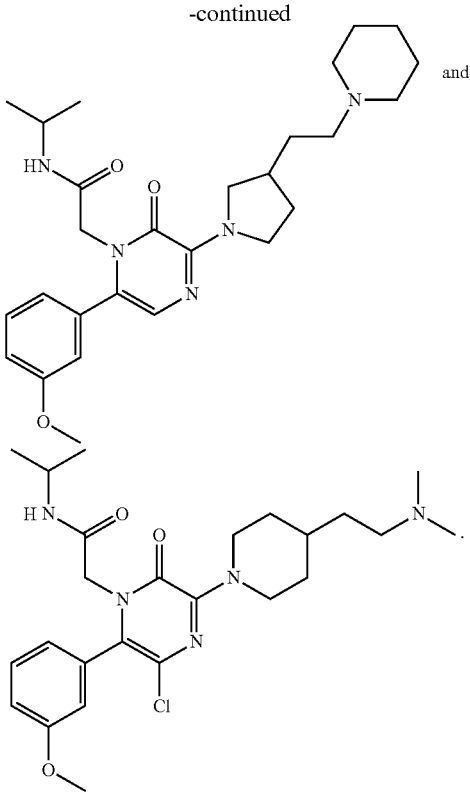

A further example: of a subgenus in accordance with embodiments of the invention is the subgenus in which R$^9$ is alkylene or similar residue (e.g. alkylene with heteroatom interruption) "tied back" into a nitrogen that is directly attached to the pyridinone, pyrimidinone or pyrazinone ring:

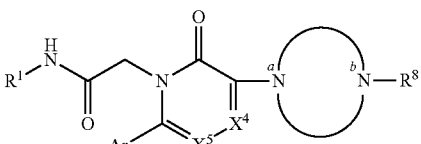

wherein

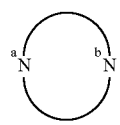

is a nitrogenous single ring heterocycle of 6 to 8 atoms or a two ring heterocycle of 9 to 13 atoms in which the nitrogen labeled b is the nitrogen of claim 1 and the nitrogen labeled a is subsumed in the definition of G. In one embodiment,

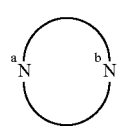

is a hexahydro-1,4diazepine ring. An example is

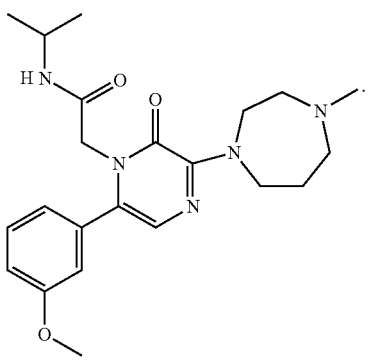

A further example of a subgenus in accordance with embodiments of the invention is the subgenus in which $R^9$ is alkylene or similar residue (e.g. alkylene with heteroatom interruption) "tied back" into a chain that is attached to the pyridinone, pyrimidinone or pyrazinone ring through an amine or amide linkage. These compounds may be thought of as a saturated nitrogenous heterocycle of 3 to 10 carbons in one or two rings attached to the pyridinone, pyrimidinone or pyrazinone ring through an alkylene chain, an amine or an amide linkage:

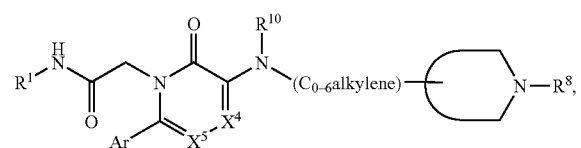

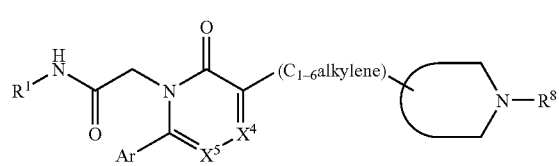

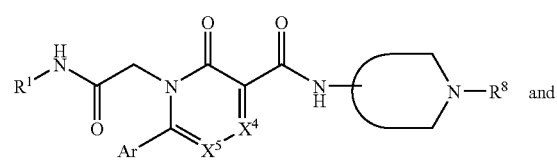

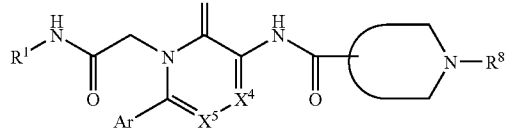

wherein

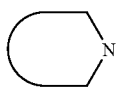

is a saturated nitrogenous heterocycle of 3 to 10 carbons in one or two rings; and $R^8$ is $C_{1-10}$ hydrocarbon. In certain embodiments,

is a piperidine ring and $R^8$ is methyl. An example is:

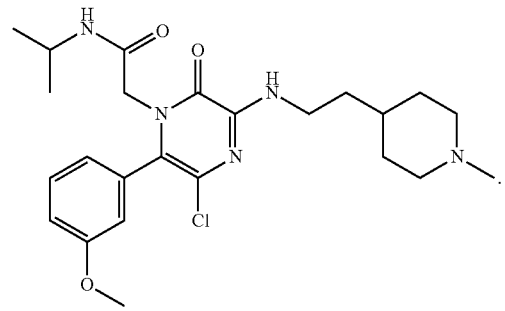 [SMILES: COc1cccc(-c2c(Cl)nc(NCCC3CCN(C)CC3)c(=O)n2CC(=O)NC(C)C)c1]

This particular subgenus also includes compounds of the formulae

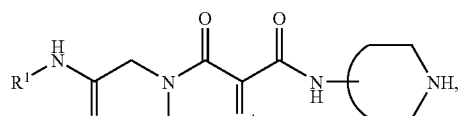

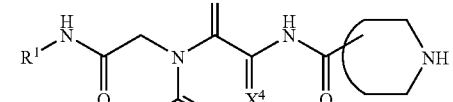

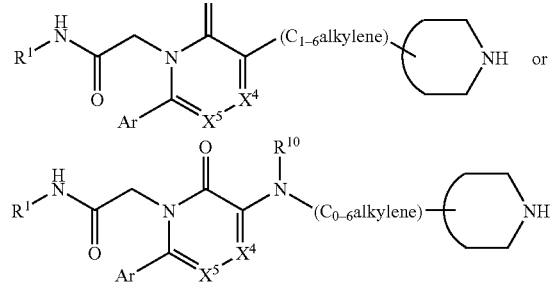

in which $R^1$ is $C_3$-$C_6$ alkyl. An example is

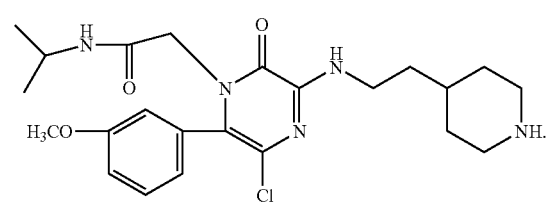 [SMILES: COc1cccc(-c2c(Cl)nc(NCCC3CCNCC3)c(=O)n2CC(=O)NC(C)C)c1]

As explained above, $R^8$ and $R^9$ may be taken together and attach to G so as to form a nitrogen-containing heterocycle.

There are three genera that, while conceptually subgenera of the genus I, may not be sensu strictu within the Markush parent structure set forth above for I. These are the pyridinones, pyrimidinones and pyrazinones formulae:

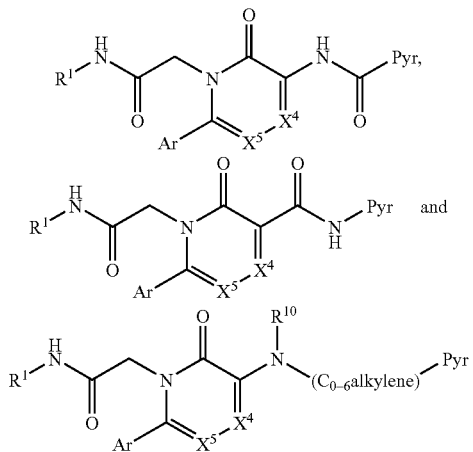

in which Pyr represents imidazole, pyridine attached through a carbon, substituted imidazole or substituted pyridine attached through a carbon. An example is:

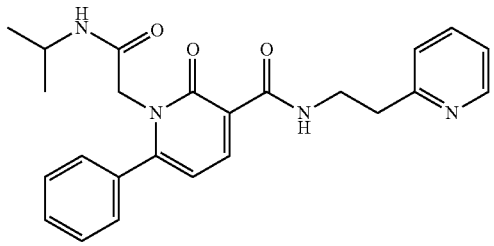 [SMILES: CC(C)NC(=O)Cn1c(-c2ccccc2)ccc(C(=O)NCCc2ccccn2)c1=O]

Among the foregoing genera, $R^1$ may be chosen from $C_{3-6}$alkyl and cycloalkyl and $C_{1-3}$alkyl substituted with phenyl, methoxy or alkynyl. For example $R^1$ may be t-butyl, isopropyl, cyclopentyl, α-methylbenzyl, methoxypropyl or propargyl. Ar may be chosen from phenyl and phenyl substituted with halogen (e.g. chloro and fluoro), $C_{1-2}$alkyl, (e.g. methyl)trifluoromethyl, $C_{1-3}$alkyloxy (e.g. methoxy), $C_{1-4}$cycloalkyloxy or trifluoromethoxy. In some embodiments, Ar is a 3-substituted phenyl ring, for example a substituted phenyl ring selected from 3-chlorophenyl, 3-fluorophenyl, 3-methoxyphenyl, 3-trifluoromethoxyphenyl, 3-chloro-4-fluorophenyl, 4-fluoro-3-methoxyphenyl and 3,5-dimethoxyphenyl.

Since the compounds in accordance with embodiments of the invention all contain a basic nitrogen, they may be presented as salts. In the claims, reference to the compound includes its salts. The term "pharmaceutically acceptable salt" refers to salts whose counter ion derives from pharmaceutically acceptable non-toxic acids and bases. Suitable pharmaceutically acceptable base addition salts for the compounds of the present invention include inorganic acids, and organic acids. Examples include acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate, and the like. When the compounds contain an acidic residue, suitable pharmaceutically acceptable base addition salts for the compounds of the present invention include ammonium, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Other base addition salts includes those made from: arecoline, arginine, barium, benethamine, benzathine, betaine, bismuth, clemizole, copper, deanol, diethylamine, diethylaminoethanol, epolamine, ethylenediamine, ferric, ferrous, glucamine, glucosamine, histidine, hydrabamine, imidazole, isopropylamine, manganic, manganous, methylglucamine, morpholine, morpholineethanol, n-ethylmorpholine, n-ethylpiperidine, piperazine, piperidine, polyamine resins, purines, theobromine, triethylamine, trimethylamine, tripropylamine, trolamine, and tromethamine.

DEFINITIONS

Throughout this specification the terms and substituents retain their definitions. Alkyl is intended to include linear, branched, or cyclic hydrocarbon structures and combinations thereof When not otherwise restricted, the term refers to alkyl of 20 or fewer carbons. Lower alkyl refers to alkyl groups of 1-6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3-8 carbon atoms. Examples of cycloalkyl groups include c-propyl, c-butyl, c-pentyl, norbornyl, adamantyl and the like. In accordance with standard nomenclature, the term "alkylene" applies to alkyl residues having two points of attachment. For example, propylene refers to —$CH_2CH_2CH_2$—.

The term "hydrocarbon" includes alkyl, cycloalkyl, alkenyl, alkynyl, aryl and combinations thereof Examples include benzyl, phenethyl, cyclohexylmethyl, camphoryl and naphthylethyl.

Alkoxy or alkoxyl refers to groups of 1-8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1-8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6-14-membered carbocyclic rings include, e.g., benzene, naphthalene, indane, tetralin, and fluorene and the 5-10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

In the characterization of the variables, it is recited that various R-groups may form rings or heterocycles. For example, $R^8$ and $R^9$ together form a 4- to 7-membered nitrogenous heterocycle. It is intended that these rings may exhibit various degrees of unsaturation, may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^3H$, $^{14}C$, $^{35}S$, $^{18}F$, and $^{36}Cl$, respectively. Compounds that contain those radioisotopes and/or other radioisotopes of other atoms are within the scope of embodiments of the invention. Tritiated, i.e. $^3H$, and carbon-14, i.e., $^{14}C$, radioisotopes are particularly known for their ease in preparation and detectability. Radiolabeled compounds of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Radiolabeled compounds are useful in screens for V3 agonists and antagonists.

The compounds described herein may contain one or more asymmetric centers and may thus give rise to enantiomers, diastereomers, and other stereoisomeric forms. Each chiral center may be defined, in terms of absolute stereochemistry, as (R)— or (S)—. Included in embodiments of the present invention are all such possible isomers, as well as their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

The abbreviations Me, Et, Ph, Tf, Ts and Ms represent methyl, ethyl, phenyl, trifluoromethanesulfonyl, toluenesulfonyl and methanesulfonyl respectively. The following abbreviations and terms have the indicated meanings throughout.

| | |
|---|---|
| abs = | absolute |
| Ac = | acetyl |
| ACN = | acetonitrile |
| Bu = | butyl |
| c- = | cyclo |
| CDI = | carbonyldiimidazole |
| conc. = | concentrated |
| DCM = | dichloromethane = methylene chloride = $CH_2Cl_2$ |
| DIC = | diisopropylcarbodiimide |
| DMAP = | 4-N,N-dimethylaminopyridine |
| DMF = | N,N-dimethylformamide |
| DMSO = | dimethyl sulfoxide |
| DPPA = | diphenylphosphoryl azide |
| dppf = | bisdiphenylphosinoferrocene |
| EDC, EDCI = | 1-ethyl-3-(3'-dimethylaminopropyl)carbodiimide |
| Et = | ethyl |
| FCC = | flash column chromatography |
| GC = | gas chromatography |
| HOAc = | acetic acid |
| HOBt = | hydroxybenzotriazole |
| i- = | iso- |
| IBCF = | isobutylchloroformate |
| IPA = | isopropyl alcohol |
| Me = | methyl |
| MP = | macroporous |
| NMM = | N-methylmorpholine |
| NMO = | N-methylmorpholine oxide |
| Ph = | phenyl |
| PhOH = | phenol |
| ppt. = | precipiate |
| PPTS = | pyridinium p-toluenesulfonate |
| Pr = | propyl |
| PS = | polystyrene |
| rt = | room temperature |
| sat'd = | saturated |
| s- = | secondary |
| t- = | tertiary |
| TBDMS = | t-butyldimethylsilyl |
| TEA = | triethylamine |
| TFA = | trifluoroacetic acid |
| THF = | tetrahydrofuran |
| TLC = | thin-layer chromatography |
| TMS = | trimethylsilyl |
| tosyl = | p-toluenesulfonyl |

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While it may be possible in accordance with some embodiments of the invention for the compounds to be administered as the raw chemical, in other embodiments the compounds are presented in a pharmaceutical composition. In accordance with an embodiment of the invention, there is provided a pharmaceutical composition comprising a compound as described herein or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend up on the condition and disorder of the recipient. The formulations may conveniently be presented in unit dosage form and may be prepared by any of the methods well known in the art of pharmacy. All methods of treatment in accordance with embodiments of the invention include the step of bringing into association a compound in accordance with embodiments of the invention or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations in accordance with embodiments of the present invention suitable for oral administration may be presented as discrete units such as capsules, cachets or tablets each containing a predetermined amount of the active ingredient; as a powder or granules, as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions in accordance with embodiments of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The dose range for adult humans is generally from 0.005 mg to 10 g/day orally. Tablets or other forms of presentation provided in discrete units may conveniently contain an amount of a compound or mixture of compounds in accordance with embodiments of the invention which is or are effective at such dosage or as a multiple of the same, for instance, units containing 5 mg to 500 mg, usually around 10 mg to 200 mg. The precise amount of compound or compounds administered to a patient will be the responsibility of the attendant physician. However, the dose employed will depend on a number of factors, including the age and sex of the patient, the precise disorder being treated, and its severity.

Compounds in accordance with embodiments of the present invention can be prepared by the following methods:

Example 1

Synthesis of Intermediate 1-4

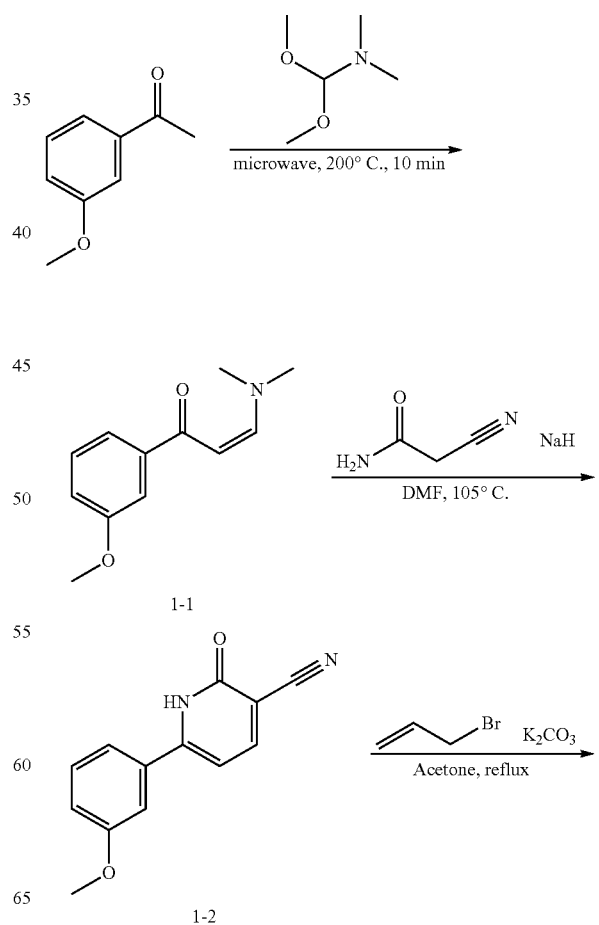

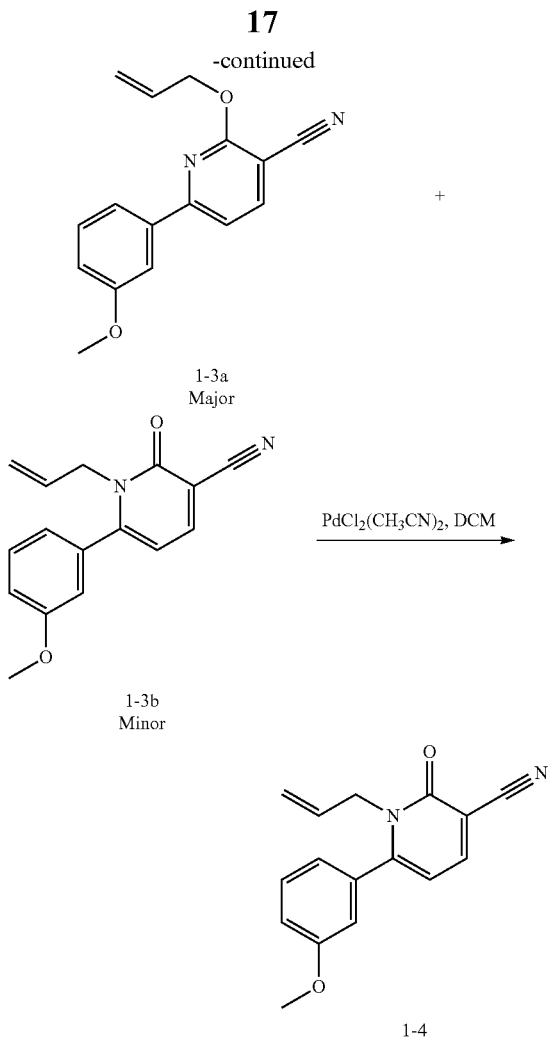

Step 3:

1-2 (28.4 g, 118.2 mmol) and potassium carbonate (49 g, 355 mmol) were combined in anhydrous acetone (400 mL) and stirred. To the stirred solution was added allyl bromide (20.5 mL; 236 mmol) and the mixture was heated to reflux with stirring for 16 h. This was conc. in vacuo and partitioned between water and DCM. The organic phase was dried over MgSO$_4$, filtered and conc. in vacuo to provide 32 g (100%) of crude product as a mixture of 1-3a (major) and 1-3b (minor). The crude residue was used in the next reaction without further purification.

Data for 1-3a: $^1$H NMR (300 MHz, CDCl3): δ 7.92 (d, 1H), 7.63-7.57 (m, 2H), 7.45-7.37 (m, 2H), 7.03 (m, 1H), 6.14 (ddt, 1H), 5.50 (d, 1H), 5.32 (d, 1H), 5.07 (d, 2H), 3.89 (s, 3H); MS (ESI), m/z (relative intensity, assignment) 267.1 (100, [M+H]$^+$).

Step 4:

To a solution of 1-3a and 1-3b from the previous step (10.5 g, 36 mmol) in DCM (150 mL) was added bis(acetonitrile) palladium(II) chloride (2.0 g, 3.6 mmol) and the reaction mixture stirred for 4 h. This was then filtered through a pad of Celite and concentrated in vacuo. The crude residue was purified by FCC (SiO2; elution with 2:1 hexanes/EtOAc) to afford 5.0 g (52%) of 1-4 as a yellow solid.

Data for 1-4: $^1$H NMR (300 MHz, CDCl3): δ 7.82 (d, 1H), 7.39 (dd, 1H), 7.04 (ddd, 1H), 6.90 (ddd, 1H), 6.85 (dd, 1H), 6.19 (d, 1H), 5.85 (ddt, 1H) 5.19 (d, 1H), 4.92 (d, 1H), 4.53 (d, 2H), 3.83 (s, 3H); MS (ESI), m/z (relative intensity, assignment) 267.1 (100, [M+H]$^+$).

Example 2

Preparation of 2-4

Step 1:

3-methoxyacetophenone (18.0 g, 120.0 mmol) and dimethylformamide dimethyl acetal (37.5 g, 315 mmol) were combined neat in a microwave reaction vessel and irradiated with microwave energy to 200° C. for 10 min. The reaction mixture was concentrated in vacuo and purified by flash column chromatography (SiO$_2$; elution with 7:3 hexane/EtOAc then 1:4.5:4.5 MeOH/EtOAc/hexane) collecting to provide 26.0 g (100%) of the enaminone 1-1 as a dark, red-orange oil.

Data for 1-1: $^1$H NMR (300 MHz, CDCl3): δ 7.75 (d, 1H), 7.41 (m, 2H), 7.23 (d, 1H), 6.95 (ddd, 1H), 5.64 (d, 1H), 3.80 (s, 3H), 3.08 (br s, 3H), 2.87 (br s, 3H), MS (ESI), m/z (relative intensity, assignment) 206.1 (100, [M+H]$^+$).

Step 2:

To a solution of 1-1 (26.8 g, 130.5 mmol) in dimethylformamide (250 mL) were added sodium hydride (60%, 6.27 g, 261 mmol) and cyanoacetamide (11.0 g, 130.5 mmol). The mixture was then stirred at 105° C. for 2 h. This was then concentrated in vacuo and the crude residue taken up in water (600 mL). The pH of the solution was adjusted with acetic acid, then warmed to 70° C. for 15 min and the resultant yellow ppt. collected by filtration. This was washed with hot water (3×150 mL) followed by cold methanol (1×500 mL) and dried overnight in a vacuum oven to provide 28.4 g (91%) 1-2 as a tan solid.

Data for 1-2: $^1$H NMR (300 MHz, DMSO$_{d6}$): δ 12.72 (br s, 1H), 8.20 (d, 1H), 7.50-7.30 (m, 3H), 7.12 (m, 1H), 6.80 (br d, 1H), 3.82 (s, 3H); MS (ESI), m/z (relative intensity, assignment) 227.2 (100, [M+H]$^+$).

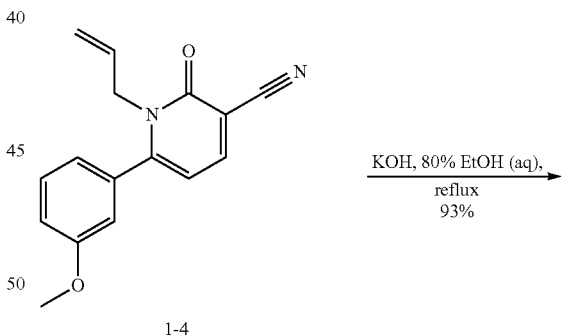

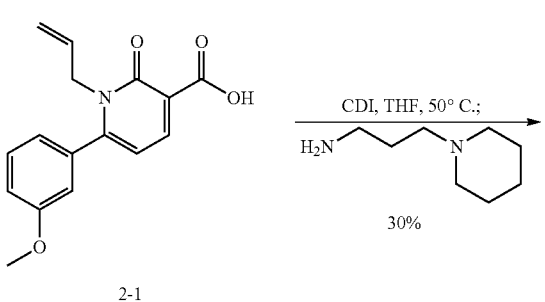

-continued

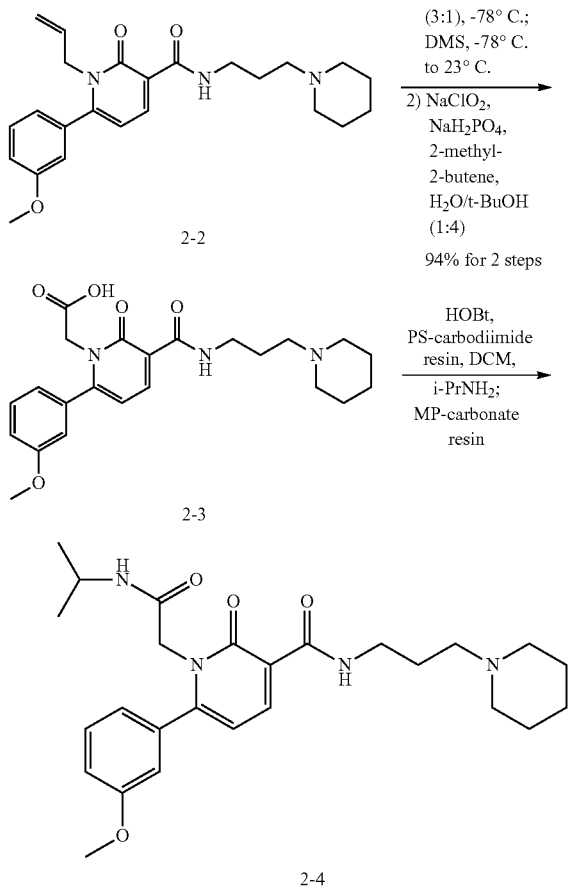

Step 1:

To a solution of 1-4 (1 g; 3.75 mmol) in 80% EtOH (aq) (10 mL) was added KOH (843 mg; 15.02 mmol). The reaction mixture was then heated to reflux for 16 h. The mixture was cooled to room temperature and partitioned between $H_2O$ (100 mL) and EtOAc (50 mL). The aq. phase was acidified to pH 3 with 2 N HCl (aq) and extracted with EtOAc (3×50 mL). The combined organic phases were dried ($MgSO_4$), filtered and conc. in vacuo giving 990 mg (93%) of 2-1.

Data for 2-1. $^1$H NMR (300 MHz, CDCl3): δ 14.3 (br s, 1H) 8.55 (d, 1H), 7.41 (dd, 1H), 7.08 (dd, 1H), 6.92 (d, 1H), 6.87 (d, 1H), 6.50 (d, 1H), 5.89 (ddt, 1H), 5.23 (d, 1H), 4.92 (d, 1H), 4.62 (d, 2H), 3.82 (s, 3H); MS (ESI), m/z (relative intensity, assignment) 286.1 (79, [M+H]$^+$).

Step 2:

To a solution of 2-1 (223 mg; 0.78 mmol) in THF (5 mL) was added CDI (253 mg; 1.56 mmol). The reaction mixture was heated to 50° C. with stirring for 2 h. The mixture was then cooled to 23° C. and 3-(piperidin-1-yl)propan-1-amine (0.7 mL; 3.9 mmol) was added. This was stirred at 23° C. for 3 h. The mixture was then partitioned between sat'd $NaHCO_3$ (aq) (50 mL) and EtOAc (3×30 mL). The combined organic phases were dried ($Na_2SO_4$), filtered and conc. in vacuo. The crude residue was purified by FCC ($SiO_2$; elution with 10% MeOH/DCM w/0.5% $NH_4OH$ (aq)) giving 97 mg (30%) of semi-pure 2-2.

Data for 2-2: MS (ESI), m/z (relative intensity, assignment) 410.2 (100, [M+H]$^+$).

Step 3:

The semi-pure amine 2-2 from step 2 (97 mg; 0.24 mmol) was taken up in DCM and treated with excess TFA then conc. in vacuo to protect the amine as a TFA salt. This was then dissolved in DCM (3 mL) and MeOH (1 mL) and cooled to −78° C. $O_3$ was bubbled through until a blueish color persisted for 5 min. A stream of Ar was then passed through the solution to remove excess $O_3$. Methyl sulfide (0.1 mL; 1.2 mmol) was added and the resultant mixture warmed to 23° C. and stirred for 16 h. The mixture was conc. in vacuo and the resultant aldehyde used crude in the next reaction.

Step 4:

The crude aldehyde from the previous step was taken up in t-BuOH (4 mL) and $H_2O$ (1 mL). To this was added $NaH_2PO_4$ (101 mg; 0.84 mmol), 2-methyl-2-butene (2.0 M in THF; 0.72 mL; 1.44 mmol) and $NaClO_2$ (80%; 35 mg; 0.312 mmol). The reaction mixture was stirred at 23° C. for 1.5 h. The mixture was then conc. in vacuo and the crude residue taken up in $H_2O$ (3 mL). This was acidified to pH 2 with 2 N HCl (aq). The mixture was then applied to a column packed with Dowex 50WX4-400 H$^+$ ion exchange resin (~10 g) and eluted with 4:1 $H_2O$/ACN until the eluent became neutral to pH paper. This was then eluted with 4:1 $H_2O$/ACN containing 10% conc. $NH_4OH$ (aq). The desired fractions containing product were combined and conc. in vacuo giving 97 mg (94% for 2 steps) of carboxylic acid 2-3.

Data for 2-3: $^1$H NMR (300 MHz, $CD_3OD$): δ 8.42 (d, 1H), 7.40 (dd, 1H), 7.12-7.03 (m, 3H), 6.45 (d, 1H), 4.45 (br s, 2H), 3.82 (s, 3H), 3.53 (t, 2H), 3.25-3.00 (m, 6H), 2.05 (pentet, 2H), 1.83 (m, 4H), 1.65 (m, 2H); LC/MS, m/z (relative intensity, assignment) 428.1 (100, [M+H]$^+$).

Step 5:

A mixture of the acid 2-3 (19 mg; 0.044 mmol), HOBt (7 mg; 0.0503 mmol) and PS-carbodiimide resin (Argonaut; 1.2 mmol/g; 49 mg; 0.0592 mmol) in DCM (1 mL) was stirred for 5 min. To this was added i-$PrNH_2$ (30 μL; 0.0296 mmol) and stirring continued for 16 h. To this was then added MP-carbonate resin (Argonaut; 2.9 mmol/g; 210 mg; 0.609 mmol) and stirring continued for 2 h. This was then filtered and conc. in vacuo giving 15.1 mg (100%) of 24.

Data for 2-4: $^1$H NMR (300 MHz, $CDCl_3$): δ 9.63 (br t, 1H, amide NH), 8.57 (d, 1H), 7.38 (dd, 1H), 7.02 (m, 3H), 6.41 (d, 1H), 5.65 (br d, 1H, amide NH), 4.45 (s, 2H), 4.08 (m, 1H), 3.82 (s, 3H), 3.48 (q, 2H), 2.38 (m, 6H), 1.81 (pentet, 2H), 1.58 (m, 4H), 1.42 (m, 2H), 1.16 (d, 6H); MS (ESI), m/z (relative intensity, assignment) 469.2 (100, [M+H]$^+$).

Example 3

Preparation of 3-3

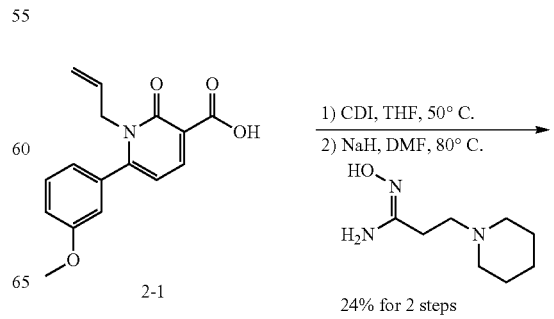

-continued

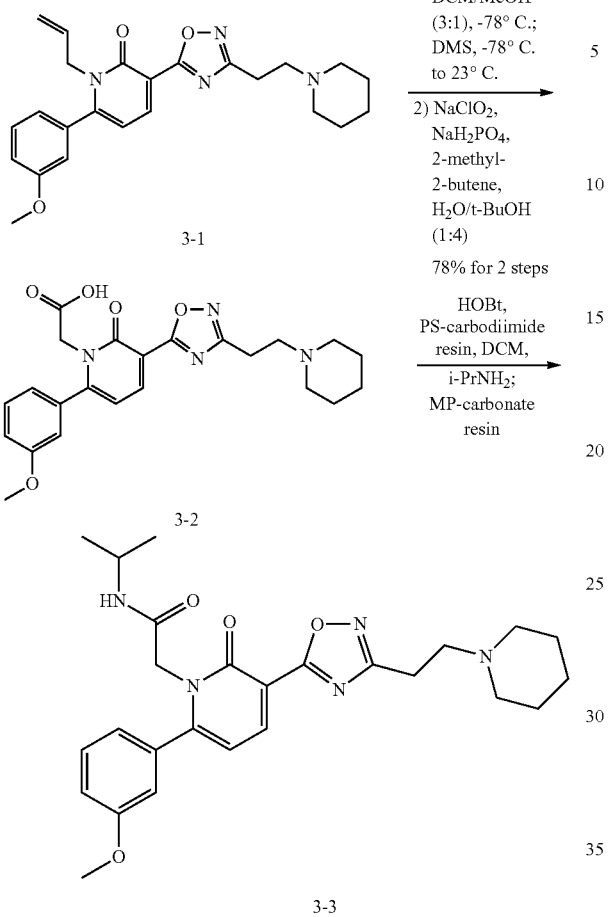

Data for 3-2: MS (ESI), m/z (relative intensity, assignment) 439.2 (100, [M+H]$^+$).

Step 4:

3-3 was prepared from acid 3-2 (25 mg; 0.057 mmol) and i-PrNH$_2$ (0.038 mmol) using the same general procedure as described in Example 2, step 5. The product was further purified by prep. HPLC giving 6.8 mg (21%) 3-3 as a TFA salt. Data for 3-3 (TFA salt): $^1$H NMR (300 MHz, CD$_3$OD): δ 8.58 (d, 1H), 7.44 (dd, 1H), 7.12 (dd, 1H), 7.04 (m, 2H), 6.61 (d, 1H), 4.62 (s, 2H), 4.03 (t, 2H), 3.92 (m, 1H, overlap with peak at 3.90), 3.90 (t, 2H, overlap with peak at 3.92), 3.81 (s, 3H), 3.61 (m, 4H), 2.13 (n, 2H), 1.93 (m, 2H), 1.76 (m, 2H); MS (ESI), m/z (relative intensity, assignment) 480.3 (100, [M+H]$^+$).

Example 4

Preparation of 4-5

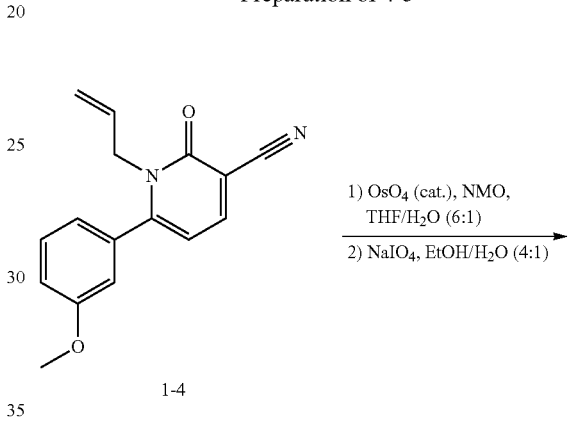

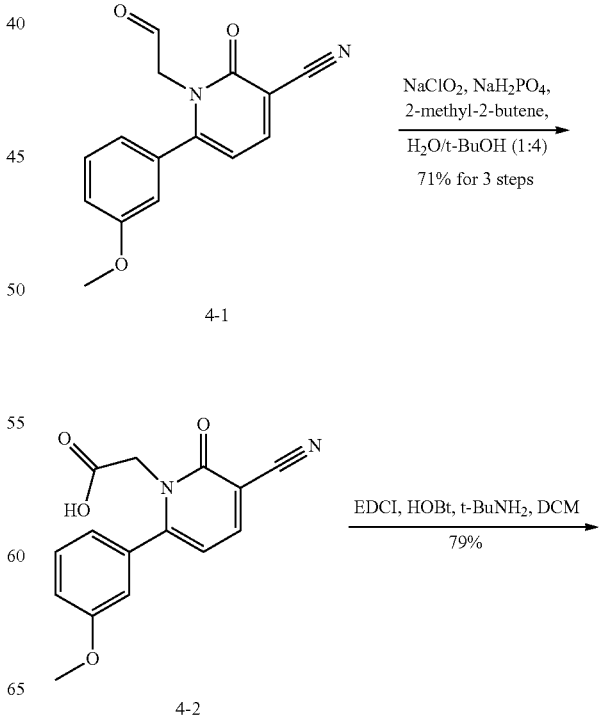

Step 1:

To a solution of acid 2-1 (442 mg; 1.55 mmol) in THF (10 mL) was added CDI (0.51 g; 3.10 mmol). The reaction mixture was heated to 50° C. and stirred for 1.5 h. The mixture was cooled, conc. in vacuo and the crude residue partitioned between EtOAc (100 mL) and H$_2$O (50 mL). The organic phase was dried (Na$_2$SO$_4$), filtered and conc. in vacuo.

NaH (60%; 65 mg; 1.63 mmol) was added to a mixture of N'-hydroxy-3-(piperidin-1-yl)propanamidine (319 mg; 1.86 mmol) and 4 Å molecular sieves (1 scoop) in DMF (10 mL) and this was stirred for 30 min at 23° C. To this was added the imidazolide from above via cannula as a soln. in DMF (3 mL w/2 mL rinse). The reaction mixture was heated to 80° C. for 3 h. The mixture was cooled and partitioned between H$_2$O (100 mL) and 3:1 DCM/i-PrOH (3×40 mL). The combined organic phases were washed with brine (1×50 mL), dried (K$_2$CO$_3$), filtered and conc. in vacuo. The crude residue was purified by FCC (SiO$_2$; elution with 10% MeOH/DCM w/0.5% conc. NH$_4$OH (aq)) giving 159 mg (24% from 2-1) of oxadiazole 3-1.

Data for 3-1: LC/MS, m/z (relative intensity, assignment) 421.2 (100, [M+H]$^+$).

Step 2 and 3:

Carboxylic acid 3-2 was prepared from alkene 3-1 (159 mg; 0.378 mmol) using the general procedures analogous to those described in Example 2, Steps 3 and 4. This afforded 130 mg (78% for 2 steps from 3-1) of acid 3-2.

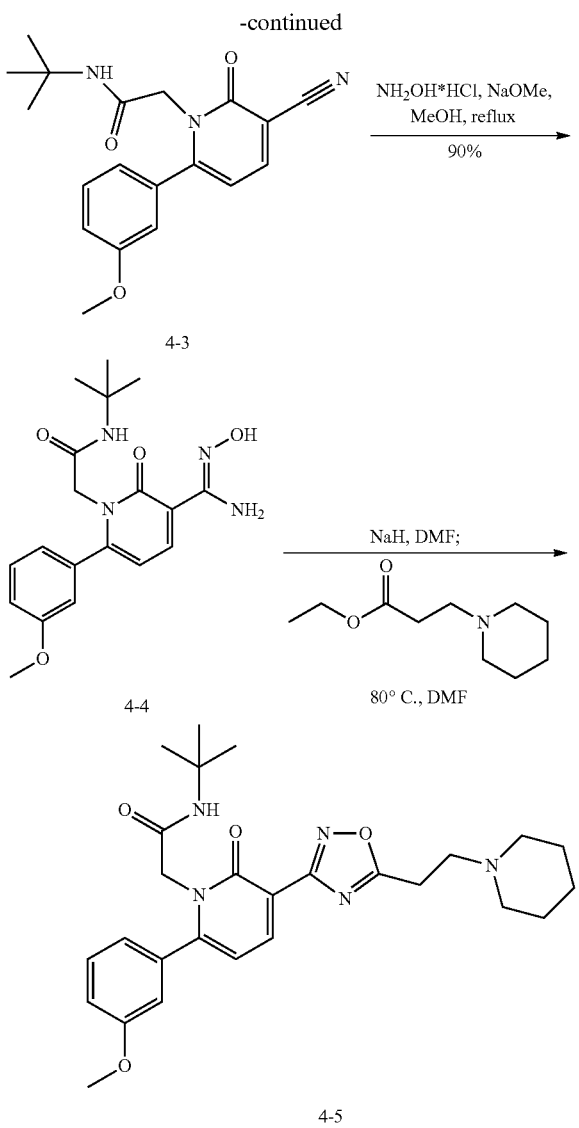

Step 1:

To a solution of 1-4 (4.5 g; 16.9 mmol) in THF (60 mL) and H$_2$O (10 mL) was added NMO (2.57 g; 21.97 mmol) and OsO$_4$ (2.5 wt. % in I-BuOH; 2.12 mL; 0.169 mmol). The reaction mixture was stirred for 16 h, then 10% Na$_2$S$_2$O$_3$ (aq) (5 mL) was added and stirred for 5 min. Three scoops of Celite were then added and the mixture filtered through a plug of Celite and conc. in vacuo. The crude residue was taken up in EtOAc (200 mL) and washed with 10% Na$_2$S$_2$O$_3$ (aq) (1×50 mL), 1 N HCl (aq) (1×50 mL) and brine (1×50 mL). The organic phase was dried (Na$_2$SO$_4$), filtered and conc. in vacuo. The desired diol was used without further purification in the next step.

Step 2:

The product diol from Step 1 was taken up in EtOH (60 mL) and to this was added NaIO$_4$ (6.51 g; 30.43 mmol) dissolved in H$_2$O (15 mL). The reaction mixture was stirred for 1 h 40 min. This was then filtered through a pad of Celite with EtOH rinses and conc. in vacuo. The crude residue was partitioned between EtOAc (200 mL) and H$_2$O (100 mL). The organic phase was dried (Na$_2$SO$_4$), filtered and conc. in vacuo. The desired aldehyde: 4-1 was used without further purification in the next step.

Data for 4-1: MS (ESI), m/z (relative intensity, assignment) 269.1 (100, [M+H]$^+$).

Step 3:

To a solution of the crude aldehyde from step 2 (~16.9 mmol) in t-BuOH (120 mL) and H$_2$O (30 mL) was added 2-methyl-2-butene (2.0 M in THF; 55.0 mL; 110 mmol), NaH$_2$PO$_4$ (7.4 g; 61.6 mmol) and NaClO$_2$ (80%; 2.21 g; 19.53 mmol). The reaction mixture was stirred at 23° C. for 1.5 h. The mixture was then conc. in vacuo and the crude residue taken up in EtOAc (200 mL) and extracted with 1 N NaOH (aq) (1×100 mL then 2×50 mL). The combined aqueous phases were then acidified with conc. HCl (aq) giving a cloudy white precipitate. This was extracted with DCM (3×100 mL). The combined organic phases were washed with brine (1×100 mL), dried (Na$_2$SO$_4$), filtered and conc. in vacuo giving 3.42 g (71% for 3 steps from 1-4) of the acid 4-2.

Data for 4-2: $^1$H NMR (300 MHz, CDCl$_3$ w/drop of CD$_3$OD): δ 7.89 (d, 1H), 7.41 (dd, 1H), 7.05 (dd, 1H), 6.94 (dd, 1H), 6.90 (dd, 1H), 6.30 (d, 1H), 4.55 (s, 2H), 3.82 (s, 3H); MS (ESI), m/z (relative intensity, assignment) 285.0 (100, [M+H]$^+$).

Step 4:

To a solution of 4-2 (1.7 g; 6.00 mmol) and t-BuNH$_2$ (0.75 mL; 7.18 mmol) in DCM (20 mL) was added EDCI (1.27 g; 6.6 mmol) and HOBt (892 mg; 6.6 mmol). The reaction mixture was stirred for 16 h. This was then diluted with EtOAc (200 mL) and washed with 1 N HCl (aq) (1×50 mL), sat. NaHCO$_3$ (aq) (1×50 mL) and brine (1×50 mL). The organic phase was dried (Na$_2$SO$_4$), filtered and conc. in vacuo. The crude residue was purified by FCC (SiO$_2$; elution with 1:1 EtOAc/hexanes) to afford 1.62 g (79%) of amide 4-3.

Data for 4-3: $^1$H NMR (300 MHz, CDCl$_3$): δ 7.83 (d, 1H), 7.38 (dd, 1H), 7.10-6.96 (m, 3H), 6.25 (d, 1H), 6.00 (br s, 1H, amide NH), 4.42 (s, 2H), 3.82 (s, 3H), 1.33 (s, 9H); MS (ESI), m/z (relative intensity, assignment) 339.8 (28, [M+H]$^+$), 267.0 (100, [M–t-BuNH]$^+$).

Step 5:

To a suspension of 4-3 (1.62 g; 4.77 mmol) in MeOH (15 mL) was added NH$_2$OH*HCl (531 mg; 7.64 mmol) and NaOMe (850 mg; 15.74 mmol). The reaction mixture was heated to reflux for 6 h. This was then cooled to room temperature and quenched with sat. NH$_4$Cl (aq) (50 mL). Extracted with 3:1 DCM/i-PrOH (3×40 mL). The combined organic phases were washed with brine (1×50 mL), dried (Na$_2$SO$_4$), filtered and conc. in vacuo giving 1.6 g (90%) of amidoxime 4-4 which was used without further purification in the next step.

Data for 4-4: LC/MS, m/z (relative intensity, assignment) 373.0 (100, [M+H]$^+$).

Step 6:

To a solution of amidoxime 4-4 (1.5 g; 4.03 mmol) in DMF (40 mL) was added NaH (60%; 145 mg; 4.83 mmol). The resultant mixture was stirred at 23° C. for 30 min. To this was added ethyl 3-(piperidin-1-yl)propanoate (1.49 g; 8.06 mmol) via cannula as a solution in DMF (5 mL). The resultant mixture was heated to 80° C. for 1.5 h. The mixture was then cooled and partitioned between H$_2$O (400 mL) and EtOAc (3×100 mL). The combined organic phases were dried (Na$_2$SO$_4$), filtered and conc. in vacuo. The crude residue was purified by FCC (SiO$_2$; elution with 5% MeOH/DCM then 10% MeOH/DCM) giving 430 mg of semipure product. This was further purified by prep. HPLC giving the TFA salt of 4-5. The TFA salt of 4-5 was treated with 10% HCl/EtOH (excess) and conc. in vacuo. This was repeated twice more to convert the TFA salt to an HCl salt. The material was then triturated with Et$_2$O giving an off-white solid which was dried in vacuo at 80° C. for 16 h. This afforded 223 mg (11%) of 45 as an HCl salt.
Data for 45 (HCl salt): $^1$H NMR (300 MHz, CD$_3$OD): δ 8.39 (d, 1H), 7.69 (br s, 1H) 7.41 (dd, 1H), 7.12-6.99 (m, 3H), 6.48 (d, 1H), 4.60 (br s, 2H), 3.81 (s, 3H), 3.75 (t, 2H, partially obscured by peak at 3.70), 3.70 (m, 2H, partially obscured by peak at 3.75), 3.56 (t, 2H), 3.10 (br t, 2H), 2.05-1.75 (m, 5H), 1.59 (m, 1H), 1.30 (s, 9H); LC/MS, m/z (relative intensity, assignment) 494.1 (100, [M+H]$^+$).
Example 5
Preparation of 5-8
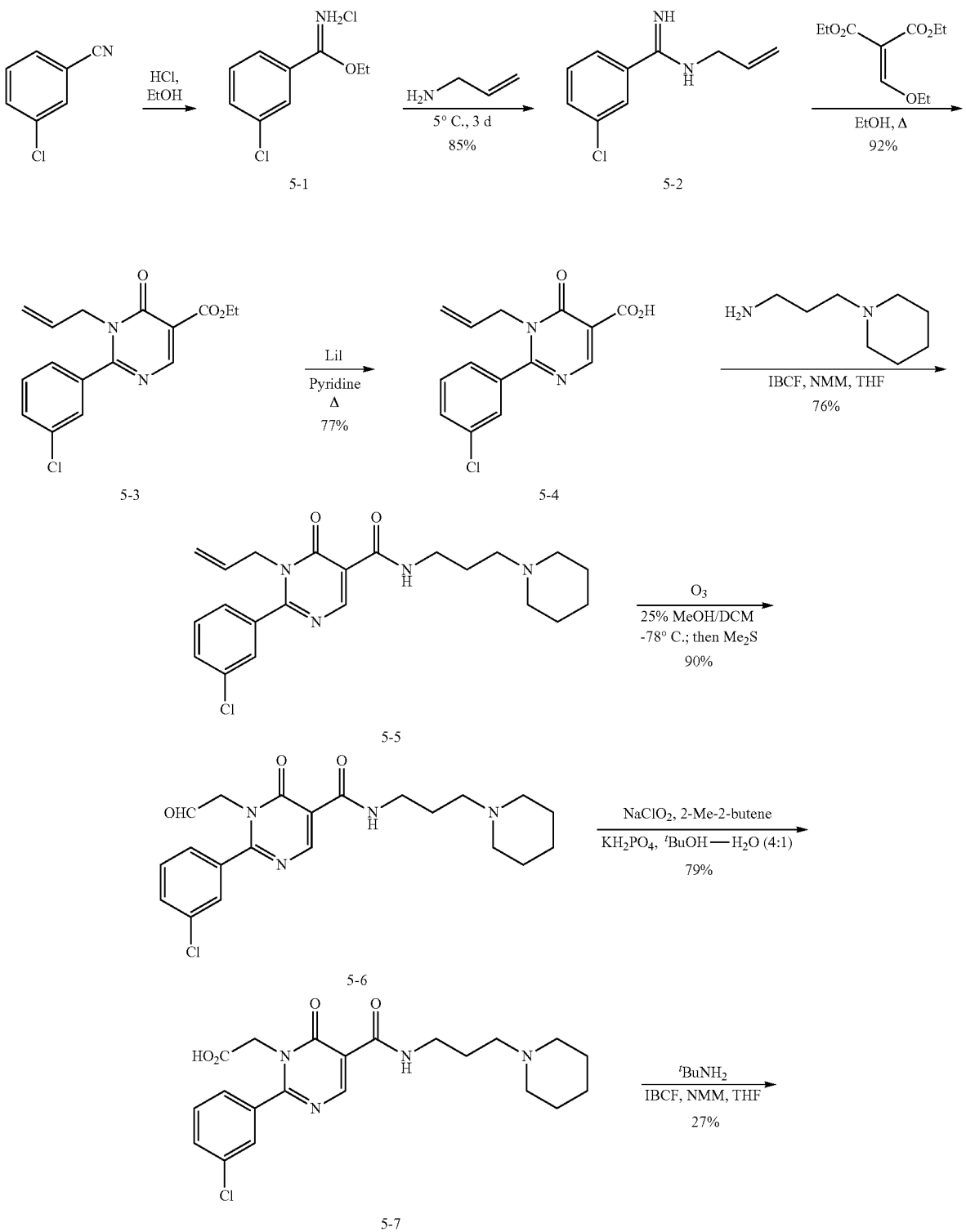

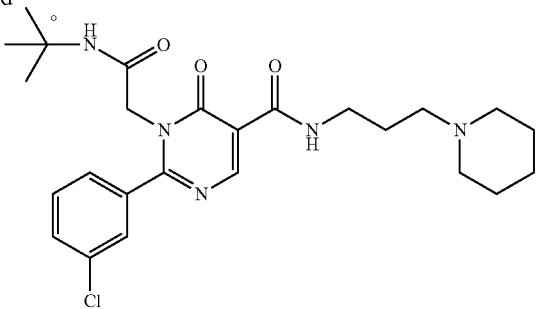

5-8

Step 1:
To a solution of 3-chlorobenzonitrile (50 g, 363 mmol) in anhydrous EtOH (500 mL), cooled to 0° C. in an ice bath, was bubbled HCl (g) through a gas dispersion tube for approximately 20 minutes until the solution was saturated. The resulting reaction mixture was stirred at room temperature for 16 h. Volatiles were removed in vacuo and the residue was triturated with anhydrous ether (~200 mL). The white solid was collected by filtration and dried in vacuo overnight yielding 80 g (100%) of 5-1.

Data for 5-1: $^1$H NMR (300 MHz, d$^6$-DMSO): δ 12.0-11.8 (br s, 1H), 8.22-8.17 (t, 1H), 8.10-8.04 (dt, 1H), 7.90-7.85 (dt, 1H), 7.71-7.64 (t, 1H), 4.66-4.50 (q, 2H), 1.55-1.40 (t, 3H).

Step 2:
To a suspension of 5-1 (18.84 g, 85.60 mmol) in methanol (anhydrous, 40 mL) at 0° C. was added allyl amine (5.38 g, 94.2 mmol), with gentle swirling, over a period of 5 min to give a homogeneous solution. The reaction flask was stoppered and allowed to stand at 5° C. for 3 d. The mixture was concentrated in vacuo to give the crude product as viscous yellow oil. The residue was partitioned between 1 N NaOH (100 mL) and DCM (4×100 mL). The combined DCM extracts were washed with brine (100 mL), dried over Na$_2$SO$_4$ and concentrated to give 15.62 g (80.1 mmol, 85%) 52 as pale yellow oil.

Data for 5-2: $^1$H NMR (CDCl$_3$): δ 7.61 (br m, 1H), 7.48 (br m, 1H), 7.40-7.31 (m, 2H), 6.00 (ddt, 1H), 5.30 (d, 1H), 5.21 (d, 1H), 3.98 (d, 2H); MS (ESI), m/z (relative intensity, assignment): 195 [100, (M+H)$^+$].

Step 3:
To a solution of 5-2 (15.6 g, 80.1 mmol) in EtOH (anhydrous, 20 mL) was added diethyl ethoxymethylenemalonate (14.6 mL, 72.9 mmol), and the resultant mixture was heated at reflux for 16 h. The mixture was concentrated in vacuo, and the residue was taken up in ethyl acetate (225 mL) and washed with sat. NH$_4$Cl (2×100 mL), H$_2$O (2×50 mL) and brine (50 mL). The combined aqueous layers were back-extracted with ethyl acetate (50 mL), and the combined organics were dried over Na$_2$SO$_4$ and concentrated to give 23.39 g (73.4 mmol, 92%) 5-3 as a red-orange, viscous oil.

Data for 5-3: $^1$H NMR (CDCl$_3$): δ 8.68 (s, 1H), 7.56-7.52 (m, 2H), 7.48-7.39 (m, 2H), 5.93 (ddt, 1H), 5.27 (d, 1H), 5.00 (d, 1H), 4.58 (d, 2H), 4.41 (q, 2H), 1.40 (t, 3H); MS (ESI), m/z (relative intensity, assignment): 319+321 (100+33, [M+H]$^+$), 658+660 (12+6, [2M+Na]$^+$).

Step 4:
To a solution of 5-3 (512 mg, 1.61 mmol) in pyridine (anhydrous, 2.3 mL) in a 5-dram vial was added lithium iodide (547 mg, 4.09 mmol). The vial was capped and the mixture was heated at 115° C. for 7.5 h. The resultant dark mixture was concentrated in vacuo, the residue was treated with 1 N HCl (5 mL) and the resultant suspension was extracted with 20% MeOH/DCM (3×5 mL). The combined organic extracts were washed with 6 N HCl (5 mL), dried over Na$_2$SO$_4$ and concentrated to give a dark brown tar. Trituration with ether gave 361 mg (1.24 mmol, 77%) of 5-4 as brown solid.

Data for 5-4: $^1$H NMR (d$^6$-DMSO): δ 13.19 (br s, 1H), 8.67 (s, 1H), 7.69-7.64 (m, 2H), 7.58 (m, 2H), 5.83 (ddt, 1H), 5.15 (d, 1H), 4.92 (d, 1H), 4.48 (d, 2H).

Step 5:
A solution of 5-4 (252 mg, 0.867 mmol) in THF (anhydrous, 5 mL) was cooled to 0° C. and N-methyl morpholine (105 µL, 0.954 mmol) was added, followed by isobutyl chloroformate (112 µL, 0.867 mmol). The mixture was stirred 2 min and N-aminopropylpiperidine (136 mg, 0.954 mmol) was added. The cooling bath was removed, and the mixture was stirred 2 h at rt. The reaction mixture was concentrated in vacuo, and the residue was partitioned between DCM (30 mL) and sat. NaHCO$_3$ (30 mL). The aqueous layer was extracted with DCM (2×10 mL) and the combined organics were washed with brine (15 mL), dried over Na$_2$SO$_4$ and concentrated to give crude product as viscous yellow oil. Flash chromatography (5% MeOH/DCM with 0.5% NH$_4$OH) afforded 275 mg (0.663 mmol, 76%) crude 5-5 as a viscous yellow oil.

Data for 5-5: MS (ESI), m/z (relative intensity, assignment): 415+417 (100+30, [M+H]$^+$).

Step 6:
Compound 5-5 was converted to the corresponding TFA salt by treatment with trifluoroacetic acid (5 mL). The salt was dissolved in 25% MeOH/DCM (10 mL) and the resultant solution was cooled to −78° C. Ozone was passed through the reaction mixture (ca. 10 min) until a blue color persisted. Oxygen was bubbled through until the blue color of ozone had faded and methyl sulfide (0.24 mL, 3.32 mmol) was added. The mixture was stirred 15 h, then washed with 1 N NaOH (5 mL). The aqueous wash was back-extracted with DCM, and the combined organic extracts were washed with brine, dried over Na$_2$SO$_4$ and concentrated to give 250 mg (0.600 mmol, 90%) crude 5-6 as viscous red oil.

Data for 5-6: MS (ESI), m/z (relative intensity, assignment): 417+419 (21+16, [M+H]$^+$), 449+451 (100+30, [M+MeOH]$^+$).

Step 7:
To a solution of 5-6 in $^t$BuOH—H$_2$O (4:1, 10 mL) was added NaH$_2$PO$_4$ (252 mg, 2.10 mmol), followed by 2-methyl-2-butene (2.0 M solution in THF, 1.8 mL, 3.6 mmol) and sodium chlorite (71 mg, 0.78 mmol). The resultant mixture was stirred 19 h at rt, then concentrated in vacuo. The residue was taken up in 2 N HCl-MeCN (5 mL) and purified by ion exchange chromatography, eluting with 20% MeCN/H$_2$O until neutral, then H$_2$O-MeCN—NH$_4$OH (4:1:0.5) to provide 204 mg (0.471 mmol, 79%) 5-7 as a white solid.

Data for 5-7: $^1$H NMR (CDCl$_3$): δ 9.51 (br t, 1H, amide NH), 8.96 (s, 1H), 7.77 (dd, 1 H), 7.59 (ddd, 1H), 7.49 (ddd, 1H), 7.44-7.37 (m, 1H), 4.49 (br s, 2H), 3.45-3.43 (br m, 4H), 2.97-2.92 (br m, 4H), 2.14-2.05 (br m, 2H), 1.91 (br m, 6H); MS (ESI), m/z (relative intensity, assignment): 433+435 (100+36, [M+H]$^+$).

Step 8:

To a solution of 5-7 (25.3 mg, 0.0584 mmol) in THF (anhydrous, 0.50 mL) was added N-methylmorpholine (7.7 μL, 0.070 mmol) and isobutyl chloroformate (7.6 μL, 0.058 mmol). The mixture was stirred 2 min and tert-butylamine (7.3 μL, 0.070 mmol) was added. Stirring was continued for 3 d, and the mixture was concentrated in vacuo. The residue was purified by reversed phase preparative HPLC to provide 9.3 mg (0.016 mmol, 27%) 5-8 as the corresponding TFA salt (white solid).

Data for 5-8 (TFA salt): $^1$H NMR (d$^4$-MeOH): δ 9.55 (br t, 1H, amide NH), 8.86 (s, 1H), 7.85 (br s, 1H, amide NH), 7.66-7.63 (m, 2H), 7.59-7.51 (m, 2H), 4.62 (s, 2H), 3.58-3.52 (m, 4H), 3.19-3.14 (t, 2H), 2.99-2.91 (td, 2H), 2.12-1.96 (m, 4H), 1.85-1.72 (m, 3H), 1.61-1.50 (m, 1H), 1.31 (s, 9H); MS (ESI), m/z (relative intensity, assignment): 489+491 (100+46, [M+H]$^+$), 999+1001 (5+2, [2M+Na]$^+$).

Example 6

Preparation of 6-8

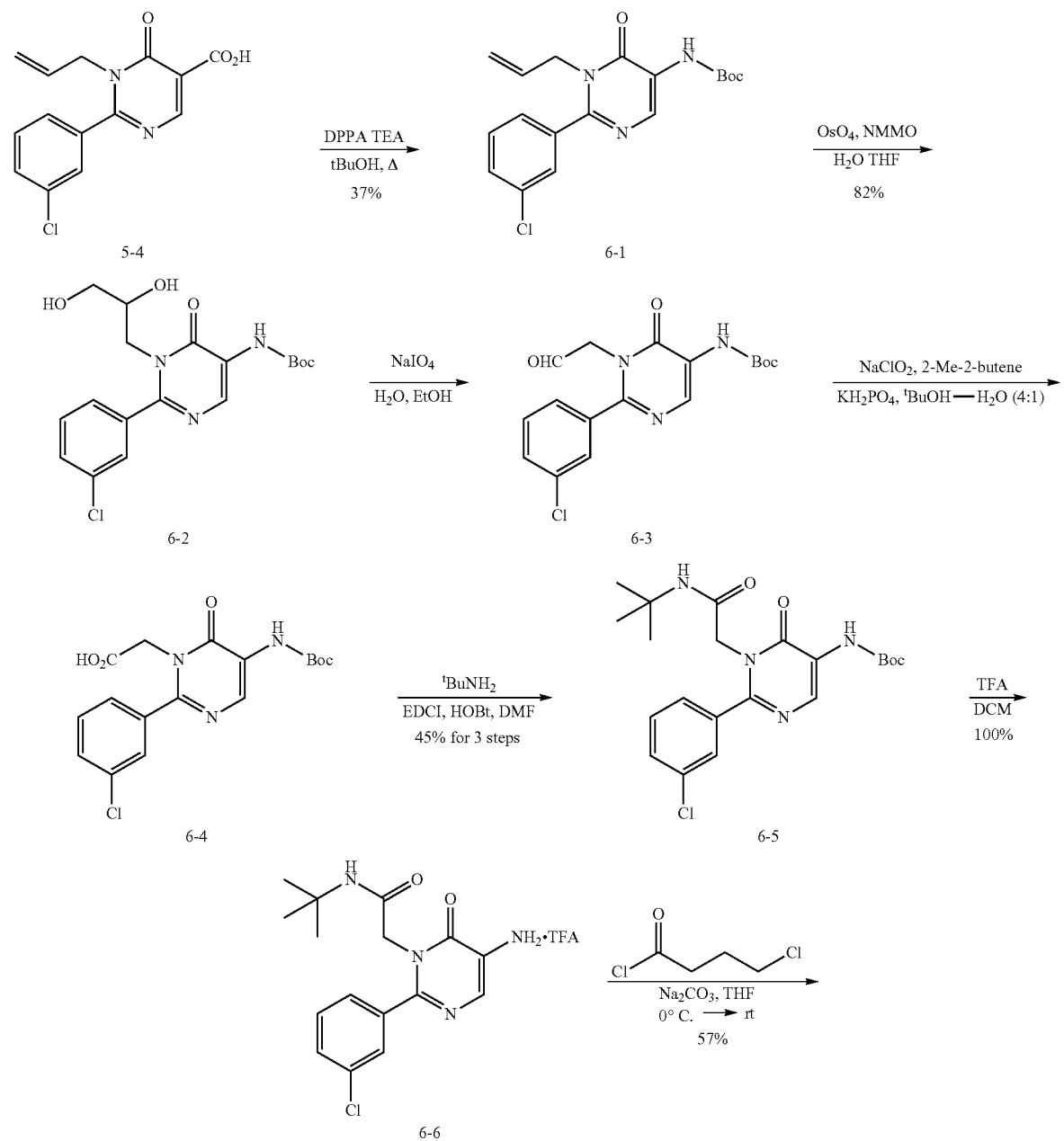

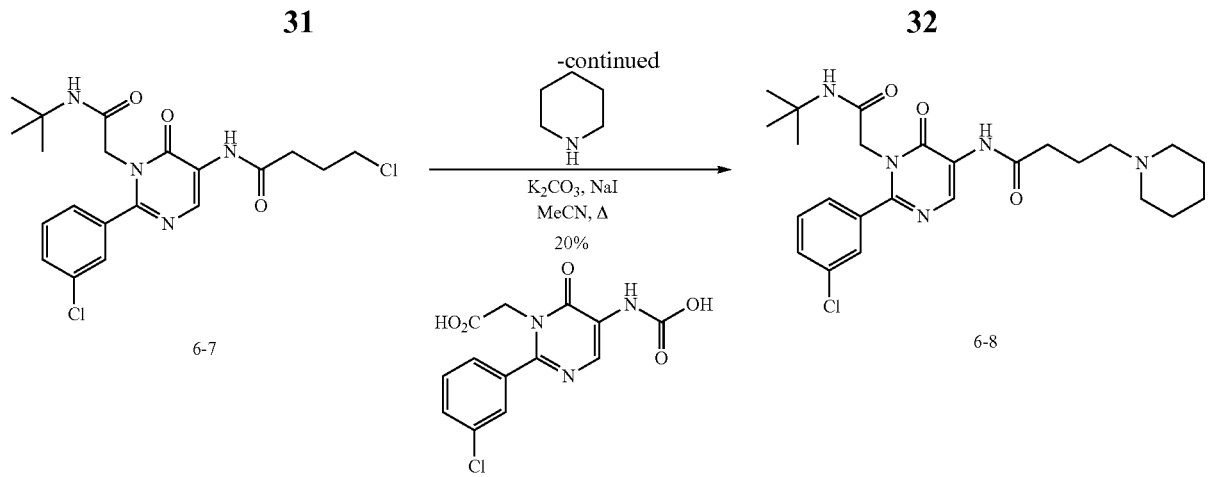

Step 1:
Compound 5-4 (820 mg, 2.82 mmol) was dried via azeotropic removal of water with toluene (2×35 mL), then taken up in tert-butanol (anhydrous, 8.5 mL). Triethylamine (0.39 mL, 2.8 mmol) and diphenylphosphoryl azide (0.61 mL, 2.8 mmol) were added, and the reaction mixture was heated at reflux for 28 h. The mixture was concentrated in vacuo and the residue was taken up in ethyl acetate (40 mL), washed with sat. $NaHCO_3$ (2×40 mL), $H_2O$ (40 mL) and brine (40 mL). The organic layer was dried over sodium sulfate and concentrated in vacuo to give the crude product as yellow-brown oil. Flash chromatography (10% ethyl acetate/hexanes) gave 379 mg (1.05 mmol, 37%) X-8 as white solid.

Data for 6-1. $^1$H NMR ($CDCl_3$): δ 8.68 (br s, 1H), 7.49-7.46 (m, 2H), 7.42-7.34 (m, 3 H), 5.87 (ddt, 1H), 5.24 (d, 1H), 4.95 (d, 1H), 4.55 (d, 2H), 1.53 (s, 9H); MS (ESI), m/z (relative intensity, assignment): 306+308 (100+32, [MH−56]$^+$), 362+364 (58+13, [M+H]$^+$).

Step 2:
To a stirred solution of 6-1 (253 mg, 0.699 mmol) in THF (6 mL) was added a solution of N-methylmorpholine oxide (119 mg, 1.02 mmol) in $H_2O$ (1 mL), followed by a 2.5% solution (w/w, 263 μL, 0.021 mmol, 3 mol %) of osmium tetroxide in tert-butanol. The resultant mixture was stirred 20 h at rt. Saturated $Na_2S_2O_3$ (aq., 1.5 mL) and Celite were added, and stirring was maintained for 30 min. The suspension was filtered, and the filter cake was washed with ethyl acetate (3×10 mL). The combined filtrates were concentrated and the residue was redissolved in 25% IPA/DCM (15 mL). The resultant solution was washed with sat. $Na_2S_2O_3$ (10 mL), 10% $NaHSO_4$ (10 mL) and brine (10 mL). The organic layer was dried over $Na_2SO_4$ and concentrated in vacuo to give 227 mg (0.573 mmol, 82%) 6-2 as white foam.

Data for 6-2: MS (ESI), m/z (relative intensity, assignment): 340+342 (100, [MH−56]$^+$), 396+398 (23+9, [M+H]$^+$), 418+420 [23+6, [M+Na]$^+$).

Step 3:
To a stirred solution of 6-2 (227 mg, 0.573 mmol) in abs. EtOH (2 mL) was added a solution of sodium periodate (245 mg, 115 mmol) in $H_2O$ (0.60 mL). The resultant milky suspension was stirred 1.5 h at rt, then filtered through Celite. The filter cake was washed with 25% IPA/DCM (3×10 mL), and the combined filtrates were concentrated in vacuo to give 302 mg (sample+residual IPA) of crude 6-3, which was immediately used in the next step without further purification.

Data for 6-3: $^1$H NMR ($CDCl_3$) δ 9.62 (s, 1H), 8.73 (br s, 1H), 7.50-7.37 (m, 5H), 4.78 (s, 2H), 1.53 (s, 9H); MS (ESI), m/z (relative intensity, assignment): 340+342 (55+14, [MH−56]$^+$), 396+398 (100+35, [M+MeOH]$^+$).

Step 4:
To a stirred solution of 6-3 in tert-butanol (9 mL) was added a solution of sodium hydrogen phosphate (202 mg, 1.68 mmol) in $H_2O$ (2 mL). To this were added $NaClO_2$ (1.3 eq) and 2-methyl-2-butene (6.0 eq). The resultant solution was stirred 20 h at rt, then concentrated in vacuo to give a white solid. The residue was partitioned between $H_2O$ (15 mL) and 25% MeOH/DCM (20 mL). The aqueous layer was extracted with 25% MeOH/DCM (2×20 mL) and the combined organic extracts were washed with brine (15 mL), dried over $Na_2SO_4$ and concentrated in vacuo to give 184 mg crude 6-4 as white solid.

Data for 6-4: $^1$H NMR ($CDCl_3$) δ 8.71 (br s, 1H), 7.50-7.34 (M, 5H), 4.60 (s, 2H), 1.53 (s, 9H); MS (ESI), m/z (relative intensity, assignment): 324+326 (51+24, [MH−56]$^+$), 380+382 (100+26, [M+H]$^+$).

Step 5:
To a stirred solution of 6-4 in DMF (anhydrous, 2.5 mL) was added tert-butylamine (56 μL, 0.53 mmol), followed by EDCI (184 mg, 0.96 mmol) and HOBt hydrate (195 mg, 1.4 mmol). The reaction mixture was stirred 16 h at rt, then partitioned between sat. $NaHCO_3$ (20 mL) and ethyl acetate (30 mL). The aqueous phase was extracted with ethyl acetate (2×25 mL), and the combined organic extracts were washed with brine (20 mL), dried over $Na_2SO_4$ and concentrated in vacuo. The residue was purified by flash chromatography (25% ethyl acetate/hexanes) to give 93.9 mg (0.216 mmol, 45% from 6-2) 6-5 as white foam.

Data for 6-5: $^1$H NMR ($CDCl_3$) δ 8.69 (br s, 1H), 7.57 (dd, 1H), 7.49-7.36 (m, 3H), 7.29 (s, 1H), 5.53 (br s, 1H), 4.42 (s, 2H), 1.52 (s, 9H), 1.35 (s, 9H); MS (ESI), m/z (relative intensity, assignment): 379+381 (22+5, [MH−56]$^+$, 435+437 (100+45, [M+H]$^+$).

Step 6:
Trifluoroacetic acid (1.5 mL) was added to a solution of 6-5 (93.9 mg, 0.216 mmol) in DCM (anhydrous, 1.5 mL). The resultant yellow solution was stirred 40 min at rt and concentrated in vacuo to give 125 mg crude 6-6 as yellow-brown foam.

Data for 6-6: MS (ESI), m/z (relative intensity, assignment): 335+337 (100, [M+H]$^+$).

Step 7:
To a stirred solution of crude 6-6 (19.9 mg, 0.046 mmol) in THF (anhydrous, 0.5 mL,) at 0° C. was added sodium carbonate (22 mg, 0.21 mmol) and 4-chlorobutyryl chloride (7.0 μL, 0.060 mmol). The reaction mixture was stirred 1 h at 0°

C., poured into sat. NaHCO₃ (1 mL) and extracted with ethyl acetate (2×3 mL). The combined organic extracts were washed with brine (2 mL), dried over Na₂SO₄ and concentrated in vacuo to give 11.5 mg (0.026 mmol, 76%) 6-7 as off-white foam.

Data for 6-7: ¹H NMR (CDCl₃) δ 9.07 (s, 1H), 8.04 (br s, 1H), 7.58 (t, 1H), 7.58-7.37 (m, 3H), 5.48 (br s, 1H), 4.44 (s, 2H), 3.66 (t, 2H), 2.64 (t, 2H), 2.20 (app quint, 2H), 1.36 (s, 9H); MS (ESI), m/z (relative intensity, assignment): 439+441 (100+58, [M+H]⁺), 461+463 (26+19, [M+Na]⁺).

Step 8:

To a stirred solution of 6-7 (11.5 mg, 0.026 mmol) in MeCN (anhydrous, 0.3 mL) was added K₂CO₃ (18 mg, 0.13 mmol), piperidine (7.0 µL, 0.080 mmol) and a catalytic amount of sodium iodide. The resultant mixture was heated 8 h at 85° C., then poured into ethyl acetate (4 mL). The layers were separated, and the aqueous phase was extracted with ethyl acetate (3×1 mL). The combined organic extracts were washed with brine (1 mL), dried over Na₂SO₄ and concentrated in vacuo. The residue was purified by preparative TLC (5% MeOH/DCM+0.5% NH₄OH, 500 µm) to give 2.5 mg (0.0051 mmol, 20%) 6-8 as a pale yellow glassy solid.

Data for 6-8: ¹H NMR (CDCl₃) δ 9.07 (s, 1H), 8.28 (br s, 1H), 7.58 (t, 1H), 7.50-7.45 (m, 3H), 5.56 (br s, 1H), 4.44 (s, 2H), 2.55-2.50 (m, 4H), 2.04-1.96 (m, 4H), 1.75-1.66 (br m, 4H), 1.51-1.40 (br m, 4H), 1.36 (s, 9H); MS (ESI), m/z (relative intensity, assignment): 488+490 (100+34, [M+H]⁺).

Example 7

Preparation of 7-4

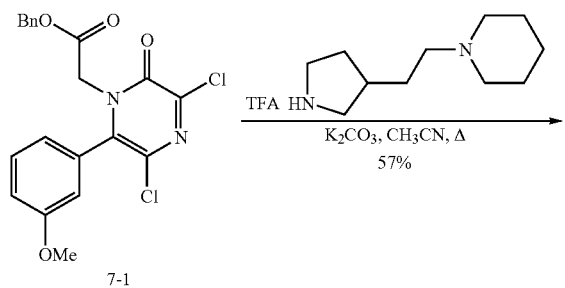

7-1

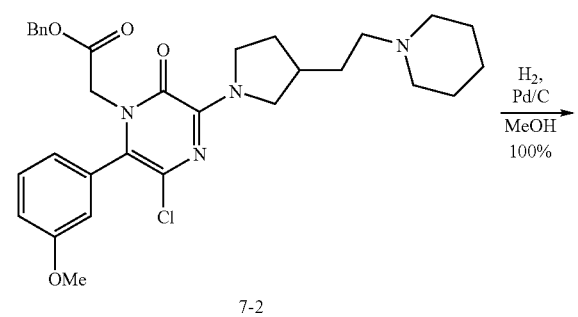

7-2

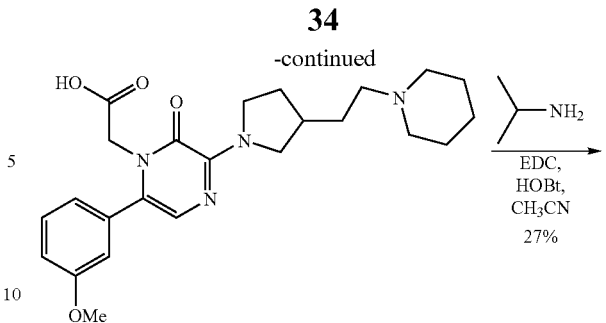

7-3

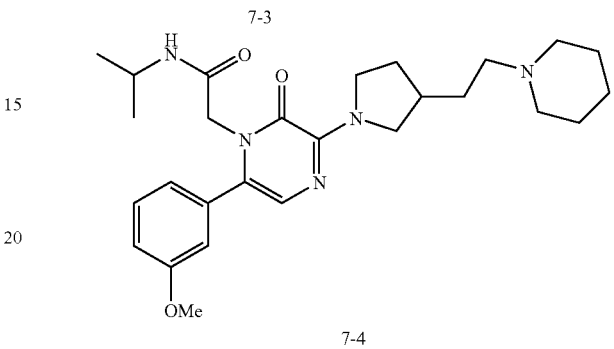

7-4

Step 1:

Compound 7-1 was prepared from literature procedures (*J. Med. Chem.*, 2003, 46, 4050-4062). To a solution of compound 7-1 (1.0 g, 2.4 mmol) in acetonitrile (25 mL) was added 1-(2-(pyrrolidin-3-yl)ethyl)piperidine trifluoroacetic acid (666 mg, 2.4 mmol) and potassium carbonate (660 mg, 2.4 mmol). The mixture was stirred at reflux for 16 h. After cooling to rt, the mixture was filtered and the filtrate was concentrated. The filtrate was then diluted with CH₂Cl₂ (30 mL) and washed with saturated brine solution. The organic layer was dried over Na₂SO₄, filtered and evaporated. The crude product was purified by flash chromatography to afford 7-2 (770 mg, 1.36 mmol, 57%).

Data for 7-2: MS (ESI), m/z (assignment): 565.3/567.3 ([M+H]⁺, 100/35).

Step 2:

To a solution of compound 7-2 (385 mg, 0.68 mmol) in methanol (2 mL) was added catalytic amount of 10% Pd/C. The reaction mixture was stirred at 50° C. under 50 psi of hydrogen for 16 h. After cooling to rt, the reaction was filtered and filtrate was evaporated to afford compound 7-3 (300 mg, 0.68 mmol, quantitative).

Data for 7-3: MS (ESI), m/z (assignment): 441.2 ([M+H]⁺, 100).

Step 3:

To a solution of compound 7-3 (100 mg, 0.23 mmol) in acetonitrile (5 mL) was added propan-2-amine (100 uL, 5 equiv.), EDCI (1.15 mmol) and HOBt (1.15 mmol). The reaction was stirred at reflux for 2 h. After cooling to rt, the mixture was filtered and the filtrate was concentrated. The filtrate was then diluted with CH₂Cl₂ (5 mL) and washed with saturated NaHCO₃ and brine. The organic layer was dried over Na₂SO₄, filtered and evaporated. The crude product was purified by preparative HPLC to afford 7-4 (30 mg, 0.062 mmol, 27%).

Data for 7-4: ¹H NMR (400 MHz, CDCl₃) δ; 7.87 (br s, 1H), 7.30 (t, 1H), 6.90–6.99 (s+d, 3H), 6.63 (s, 1H), 4.29 (s, 2H), 3.99 (septet, 1H), 3.85-3.77 (m+s, 7H), 3.55 (br m, 2H), 3.09 (br m, 2H), 2.69 (br m, 2H), 2.34–2.23 (m, 2H), 1.50~2.20 (m, 8H), 1.42 (br s, 1H), 1.08 (d, 6H); MS (ESI), m/z (assignment): 482.2 ([M+H]+, 100).

Example 8

Preparation of 8-3

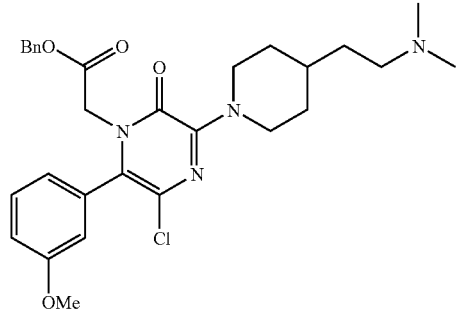
8-1

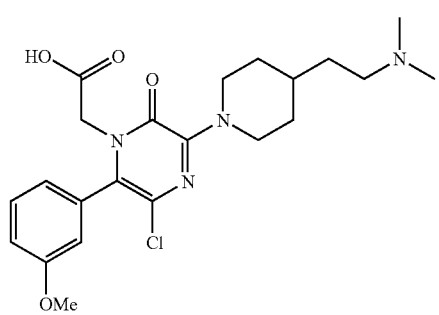
8-2

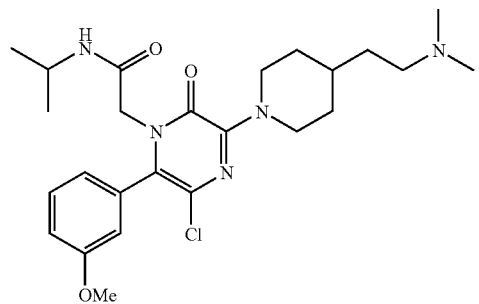
8-3

Compound 8-1 was prepared from similar procedures in Example 7. To a solution of 8-1 (90 mg, 0.17 mmol) in methanol (2 mL) was added 10% Pd/C (catalytic amount). The reaction was stirred under 1 atm of hydrogen for 16 h. The mixture was filtered and evaporated to afford 8-2 (70 mg, 0.16 mmol, 94%). Compound 8-2 was coupled with isopropylamine by using the same procedures in Example 7 to give 8-3.

Data for 8-3: MS (ESI), m/z (assignment): 490/492 ([M+H]+, 100/35).

Scheme for pyridone, IV:

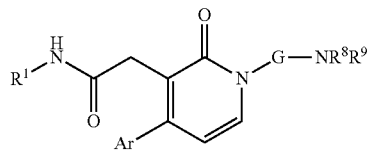
IV

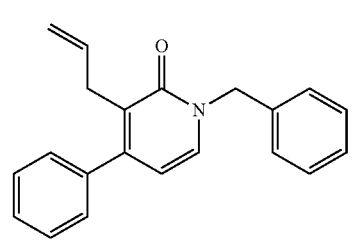
A
Synthesis described in Lin et al
J. Org. Chem. 2003, 68, 5688

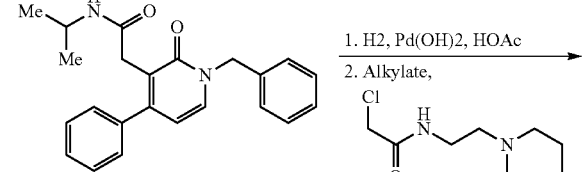

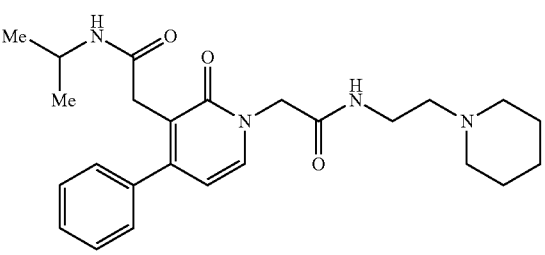

Other compounds may be prepared by modifying the synthesis of starting material A, for example to prepare

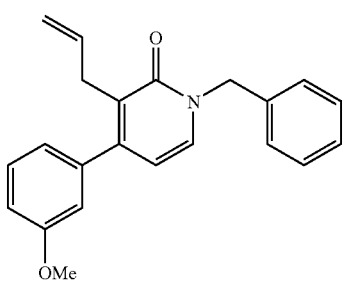 [SMILES: C=CCc1c(-c2cccc(OC)c2)ccn(Cc2ccccc2)c1=O]

as the starting material. The article of Lin et al., J. Org. Chem., 2003, 68:5688, is incorporated herein by reference.

Scheme for pyridazin-3-one VI:
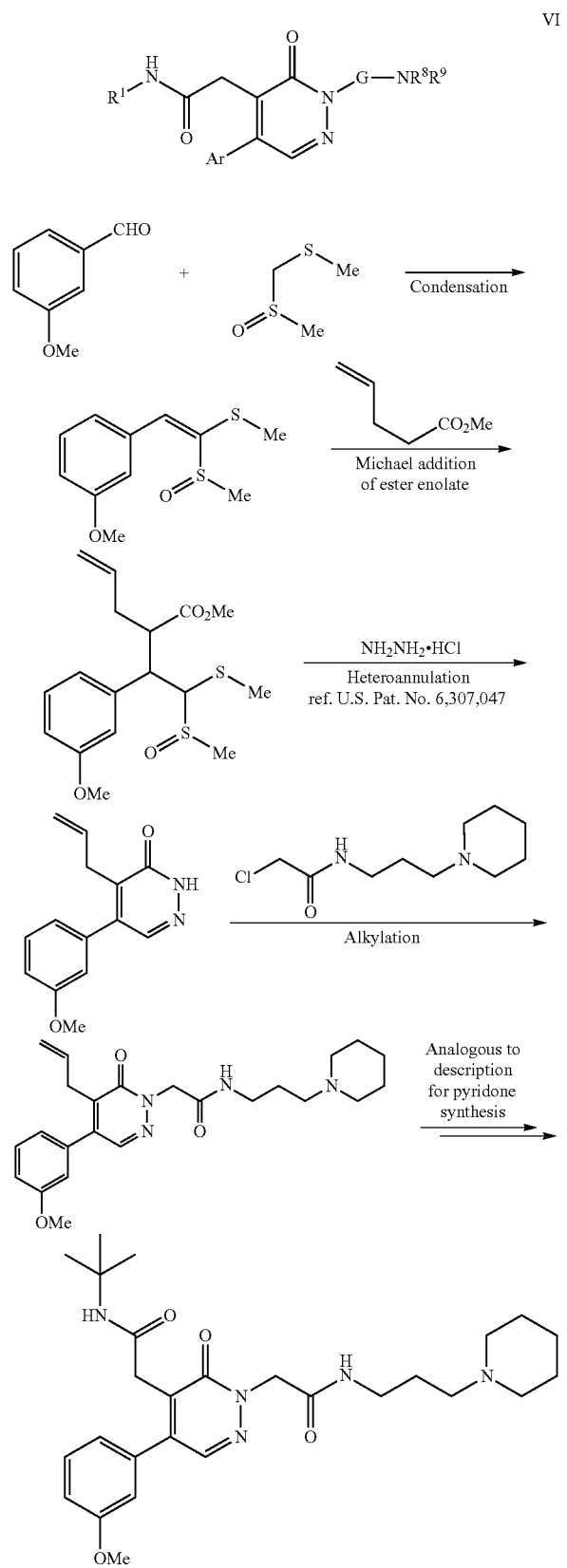
Scheme for phenyl VII:
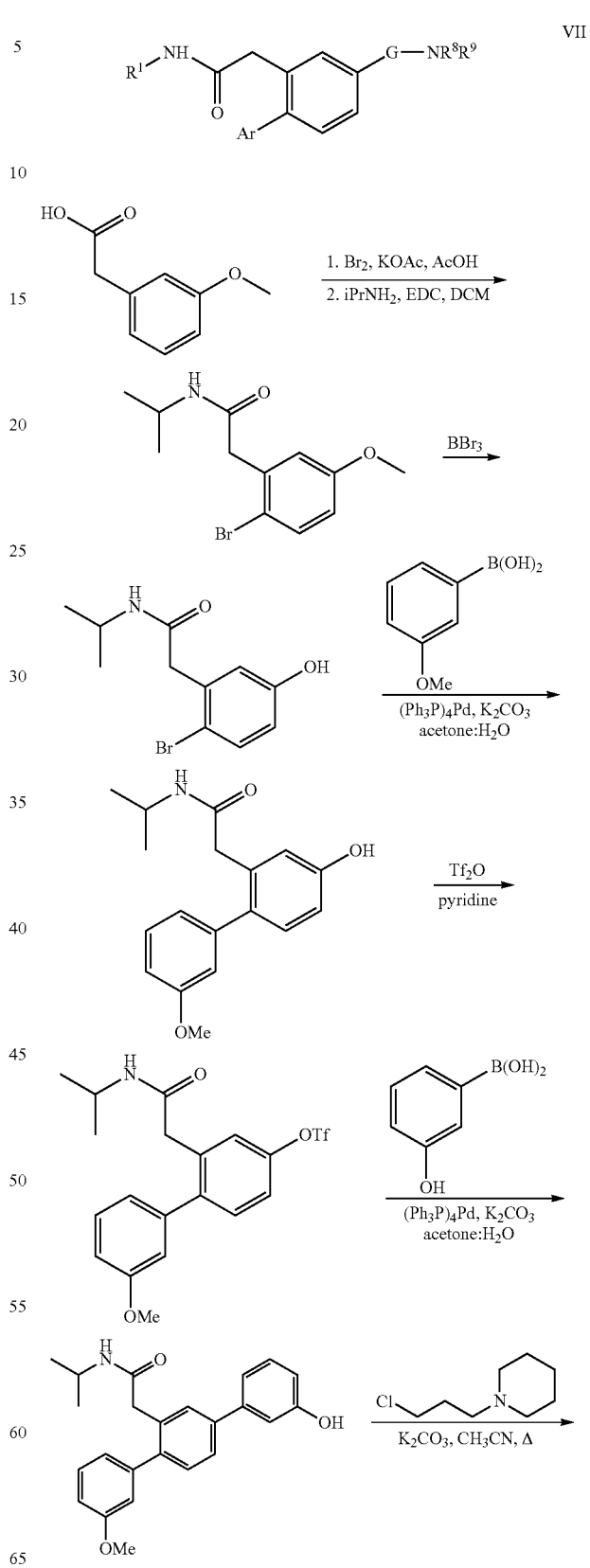

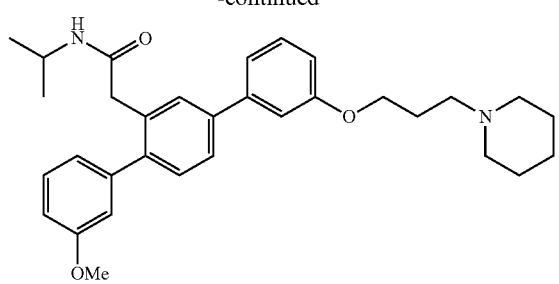
Bromination in first step see JACS, 123(15), 3434-3440; 2001
U.S. Pat. No. 6,307,047 and the article from J. Am. Chem. Soc., 123(15):3434-3440 (2001) are incorporated herein by reference.
Scheme for pyridine VIII:
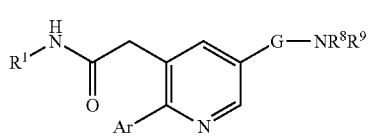
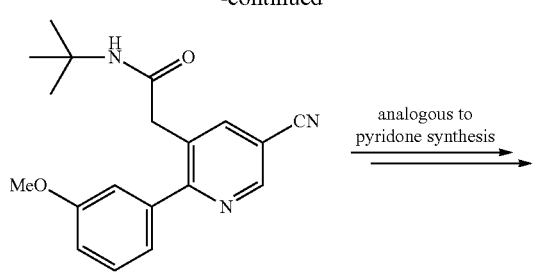
The articles from Org. Lett. 2000, 2, 2339-41 and Org. Lett. 6(17)2837-2840 are incorporated herein by reference.
Scheme for pyrimidine IX:
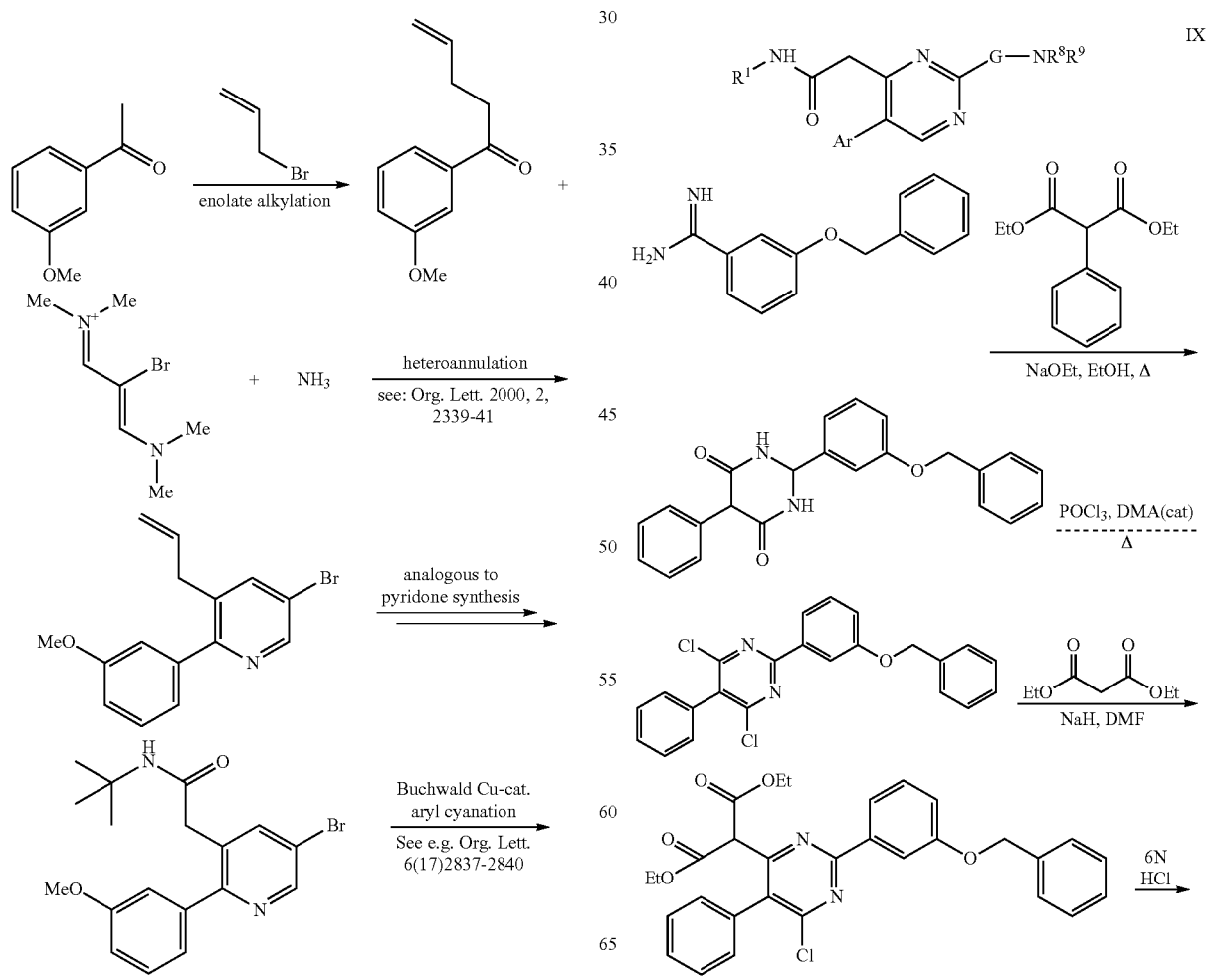

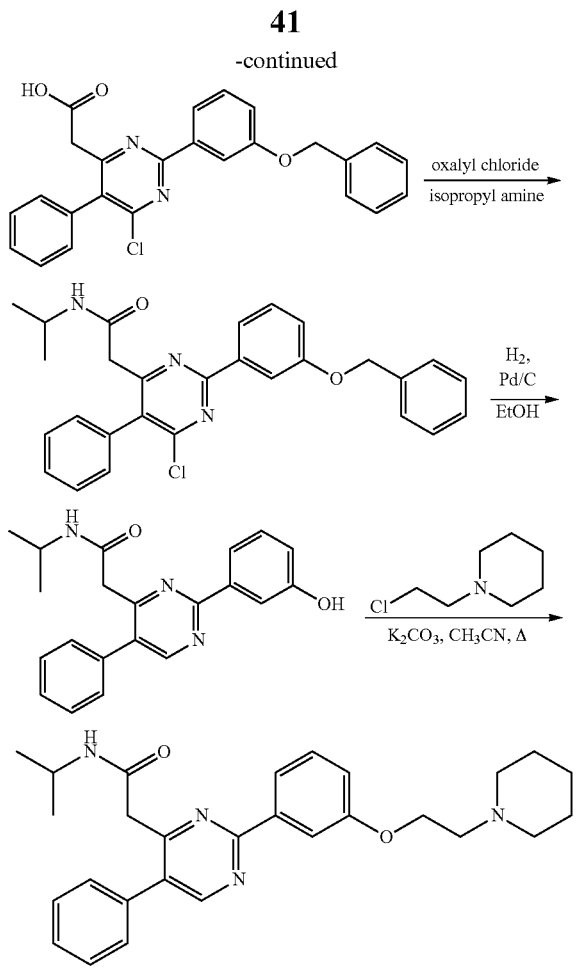

Scheme for pyrazine X:

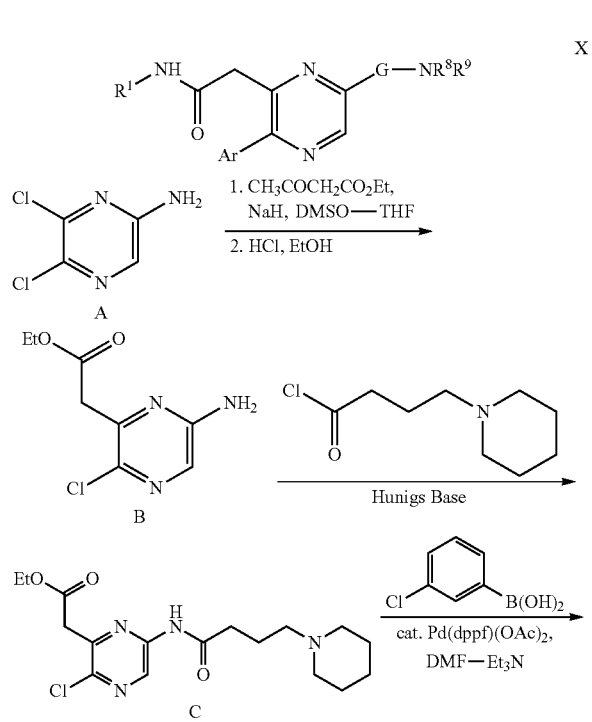

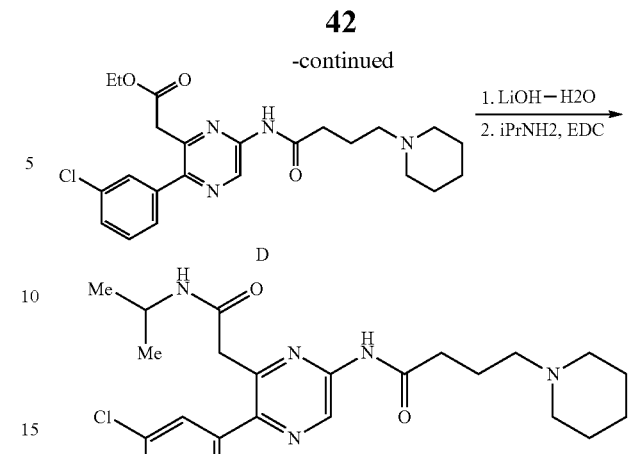

Compound A reported in Miesel et al, U.S. Pat. No. 4,160,834
Transformation analogous to A to B and C to D reported in Thompson et al, J. Org. Chem. 1988, 53, 2052-2055

U.S. Pat. No. 4,160,834 and the article of Thompson et al., J. Org. Chem. 1988, 2052-2055 are incorporated herein by reference.

Assay:

Chinese Hamster Ovary (CHO) cells stably expressing the human $V_3$ receptor were incubated to equilibrium with the test compound (at a final assay concentration of $10^{-10}$ mol·L$^{-1}$ to $10^{-4}$ mol·L$^{-1}$) and [$^3$H]AVP (at a final assay concentration of $5\times10^{-9}$ mol·L$^{-1}$). Throughout the concentration of dimethylsulphoxide (DMSO) did not exceed 1% (v/v). After washing with room temperature phosphate buffered saline (PBS), scintillation fluid was added and the plates counted on a Micro Beta Trilux counter. A sigmoidal dose response curve (non-linear regression, variable slope) was plotted as concentration of test compound (mol·L$^{-1}$) against percentage specific binding of [$^3$H]AVP and an IC$_{50}$ value was calculated.

Table 1 shows compounds that exhibited IC$_{50}$ less than 10 µM:

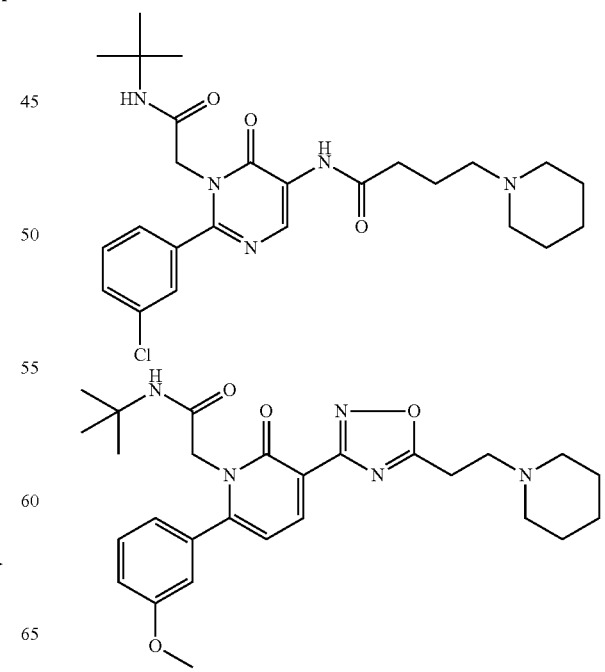

43
-continued
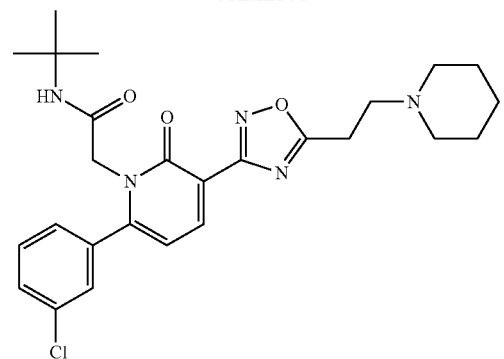
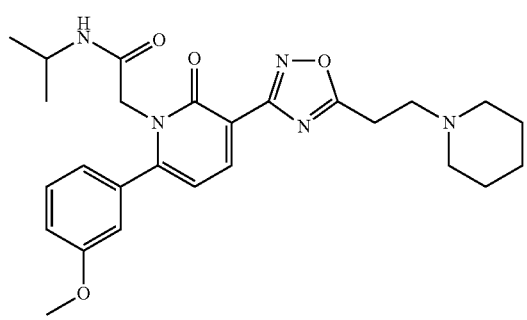
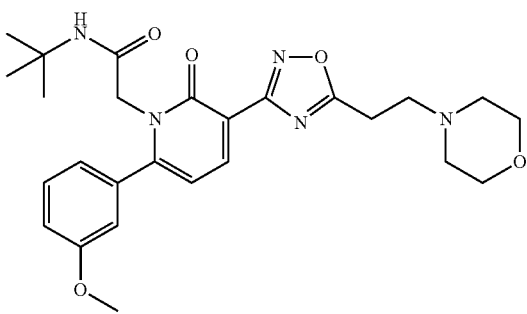
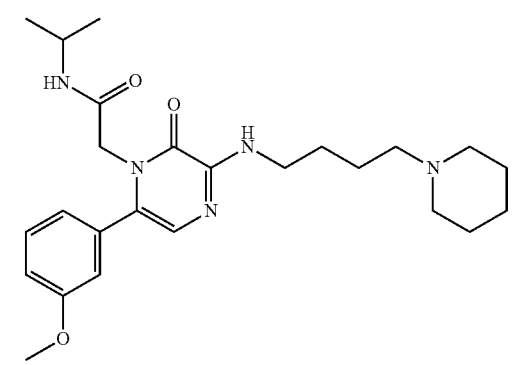
44
-continued
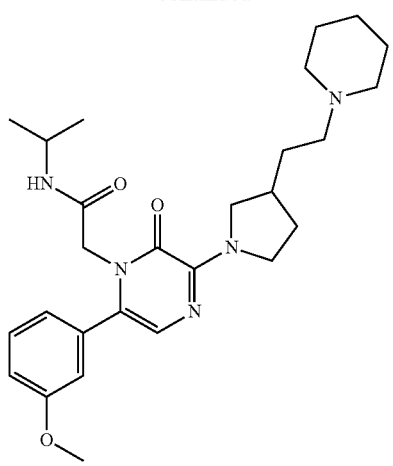
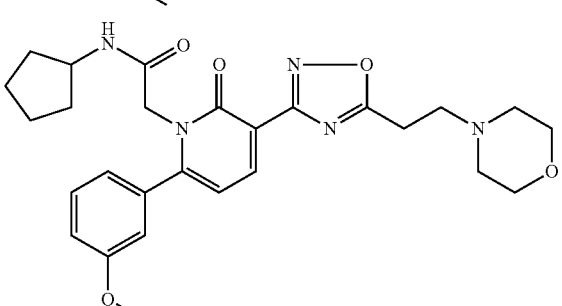
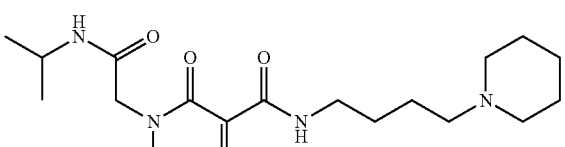
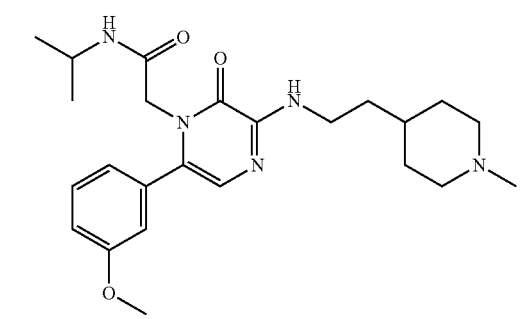

45
-continued
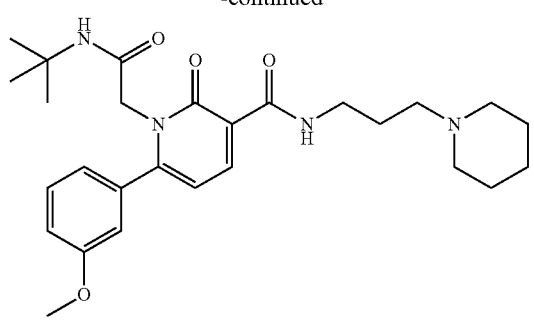
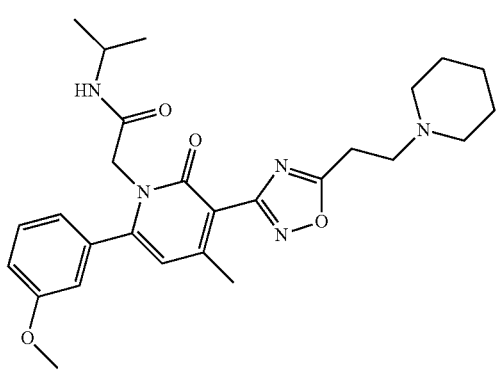
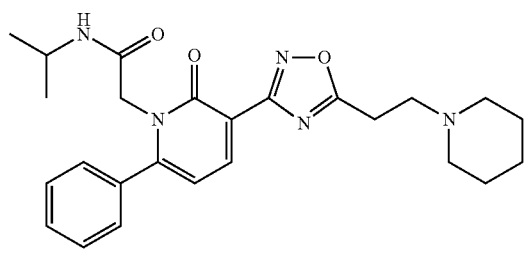
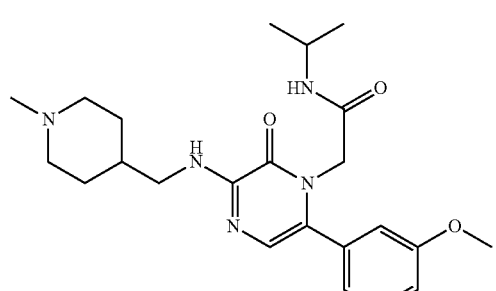
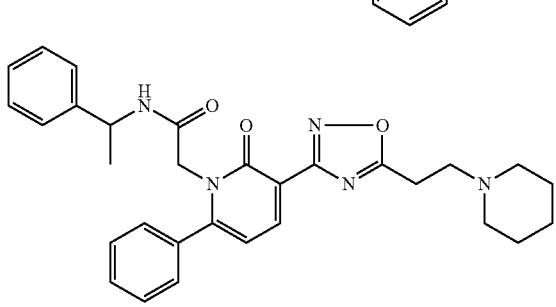
46
-continued
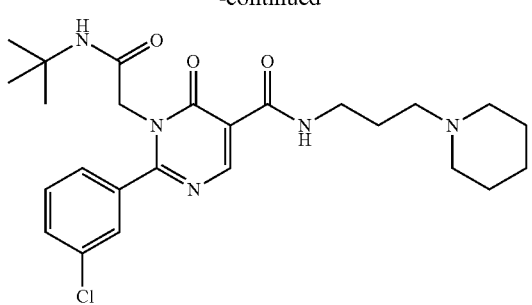
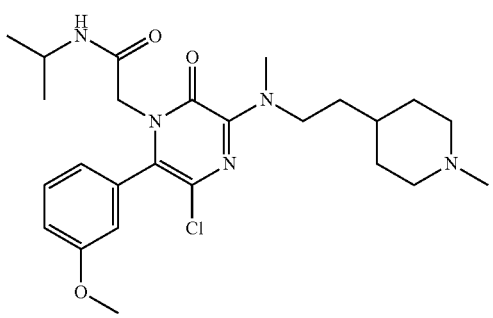
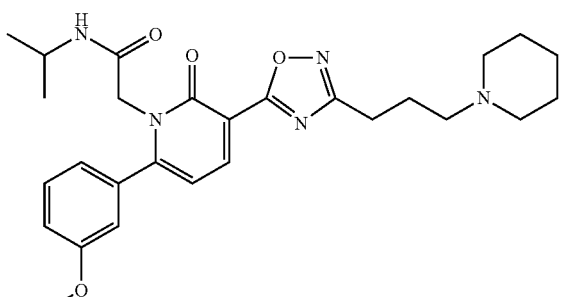
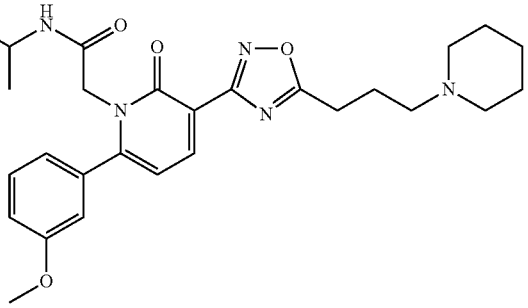
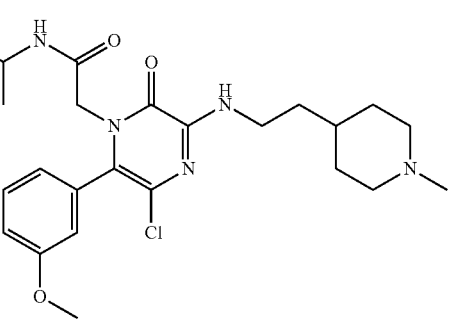

47
-continued
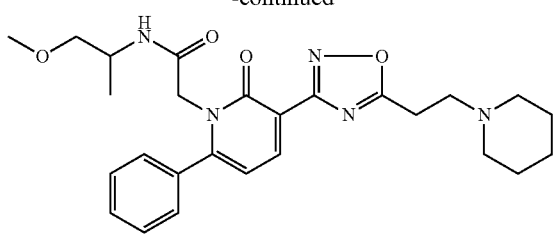
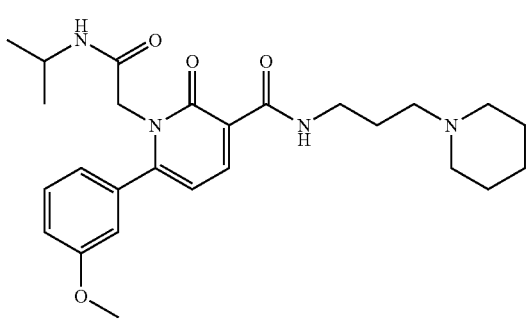
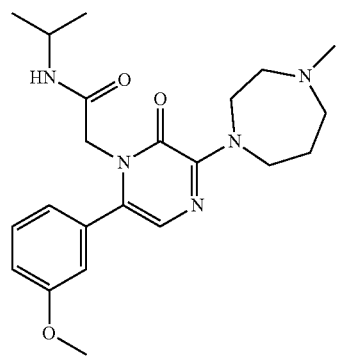
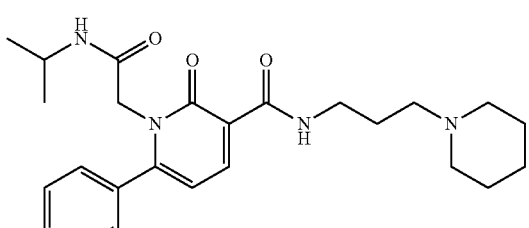
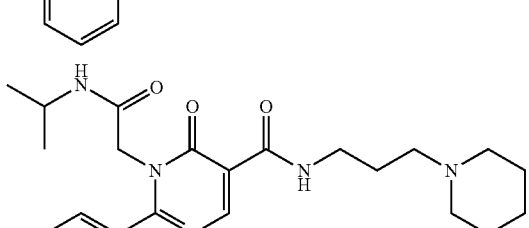
48
-continued
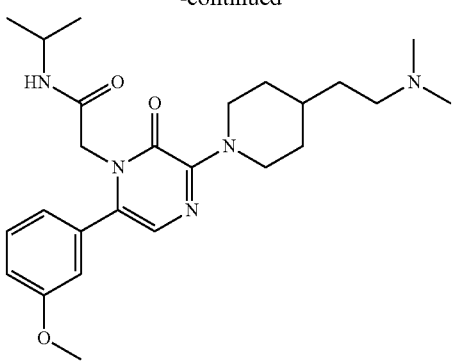
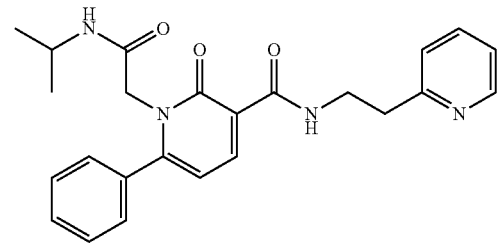
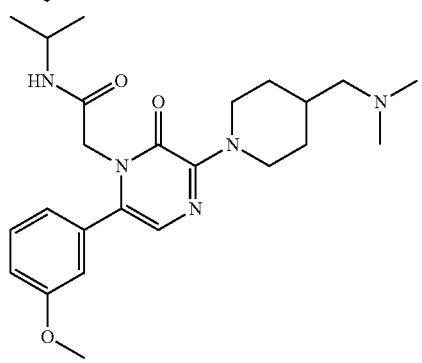
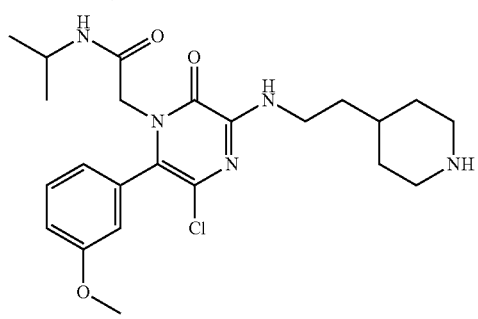
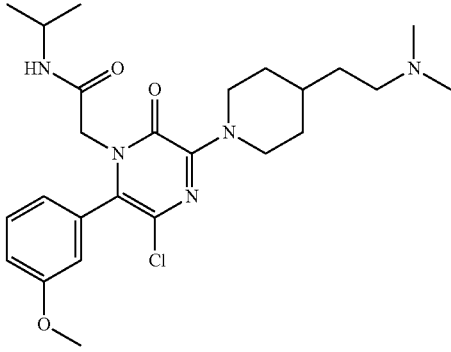

-continued

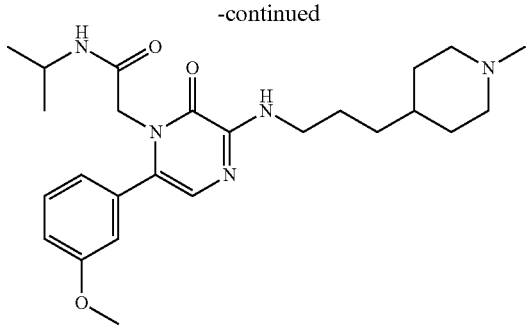

We claim:
1. A compound of formula:

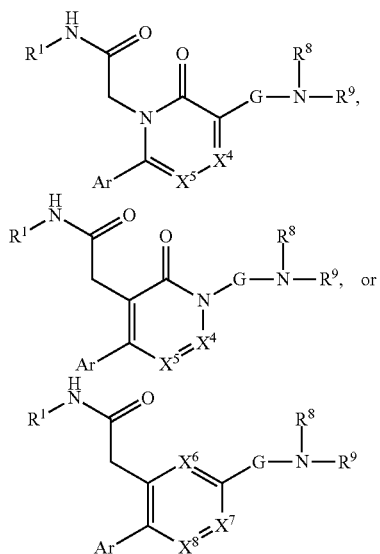

or a pharmaceutically acceptable salt thereof, wherein
$X^4$-$X^5$ is chosen from $CR^4$—$CR^5$;
one of $X^6$, $X^7$ and $X^8$ is N and the other two are $CR^4$ and $CR^5$;
$R^1$ is chosen from $(C_{1-10})$alkyl, $(C_{3-10})$cycloalkyl, and $[(C_{3-10})$cycloalkyl$(C_{1-2})$alkyl$]$, said $(C_{1-10})$alkyl, $(C_{3-10})$cycloalkyl, and $[(C_{3-10})$cycloalkyl$(C_{1-2})$alkyl$]$ being optionally substituted with one or more halogens, $(C_{1-6})$alkoxy, $(C_{2-6})$alkenyl, $(C_{2-6})$alkynyl, phenyl or benzyl;
Ar is chosen from
(i) $(C_{6-10})$aryl, optionally substituted within 1-3 substituents selected from halogen, hydroxy, cyano, COOR$^5$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens;
(ii) $(C_{5-10})$heteroaryl optionally substituted with a substituent selected from methyl, $(C_{1-6})$alkyloxy or halogen; and
(iii) $(C_{4-7})$cycloalkyl;
$R^4$ and $R^5$ are independently chosen from H, $(C_{1-6})$alkyl, $(C_{1-6})$alkyloxy or halogen, said $(C_{1-6})$alkyl, $(C_{1-6})$alkyloxy being optionally substituted with one or more halogens;

G is a linking moiety spanning 4 to 7 atoms between termini; and
$R^8$ and $R^9$ are hydrogen or alkyl, or NR$^8$R$^9$ is a saturated nitrogenous heterocycle of 3-10 carbons in one or two rings.
2. A compound according to claim 1 or a pharmaceutically acceptable salt thereof, wherein G is a linking moiety spanning 4 to 7 atoms between termini, said linking moiety incorporating at least one of
(a) an sp2 hybridized carbon,
(b) a cyclic structure, and
(c) when the nitrogen bearing $R^8$ and $R^9$ is part of a 4- to 7-membered nitrogenous heterocycle, G may additionally be —$(C_{4-7})$alkylene or —N($R^{10}$)—$(C_{3-6})$alkylene; and $R^{10}$ is H or $(C_{1-6})$alkyl.
3. A compound according to claim 1 or a pharmaceutically acceptable salt thereof, wherein at least one of $R^8$ and $R^9$ is other than hydrogen.
4. A compound of formula

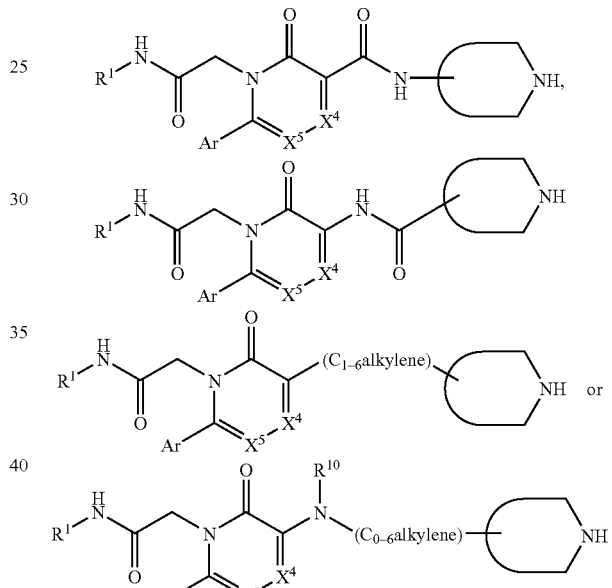

or a pharmaceutically acceptable salt thereof, wherein
$R^1$ is $C_3$-$C_6$ alkyl;
$X^4$-$X^5$ is $CR^4$—$CR^5$;
$R^4$ and $R^5$ are independently chosen from H, $(C_{1-6})$alkyl, $(C_{1-6})$alkyloxy or halogen, said $(C_{1-6})$alkyl, $(C_{1-6})$alkyloxy being optionally substituted with one or more halogens;
Ar is chosen from
(i) $(C_{6-10})$aryl, optionally substituted with 1-3 substituents selected from halogen, hydroxy, cyano, COOR$^5$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens;
(ii) $(C_{5-10})$heteroaryl optionally substituted with a substituent selected from methyl, $(C_{1-6})$alkyloxy or halogen; and
(iii) $(C_{4-7})$cycloalkyl; and $R^{10}$ is H or $(C_{1-6})$alkyl;
and

is a saturated nitrogenous heterocycle of 3 to 10 carbons in one or two rings.

5. A compound according to claim 1 or a pharmaceutically acceptable salt thereof, wherein both of $R^8$ and $R^9$ are other than hydrogen.

6. A compound of formula:

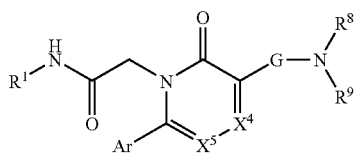

or a pharmaceutically acceptable salt thereof, wherein
$X^4$-$X^5$ is chosen from $CR^4$=$CR^5$;
$R^1$ is chosen from $(C_{1-10})$alkyl, $(C_{3-10})$cycloalkyl, [$(C_{3-10})$cycloalkyl($C_{1-2}$)alkyl], said $(C_{1-10})$alkyl, $(C_{3-10})$cycloalkyl, and [$(C_{3-10})$cycloalkyl($C_{1-2}$)alkyl] being optionally substituted with one or more halogens, $(C_{1-6})$alkoxy, $(C_{2-6})$alkenyl, $(C_{2-6})$alkynyl, phenyl or benzyl;
Ar is $(C_{6-10})$aryl, optionally substituted with 1-3 substituents selected from halogen, hydroxy, cyano, $COOR^5$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens, or Ar is a $(C_{5-10})$heteroaryl optionally substituted with a substituent selected from methyl, $(C_{1-6})$alkyloxy or halogen or $R^2$ is $(C_{4-7})$cycloalkyl;
$R^4$ and $R^5$ are independently chosen from H, $(C_{1-6})$alkyl, $(C_{1-6})$alkyloxy or halogen, said $(C_{1-6})$alkyl, $(C_{1-6})$alkyloxy being optionally substituted with one or more halogens;
$R^8$ and $R^9$ are hydrogen or alkyl, or $NR^8R^9$ is a 4- to 7-membered nitrogenous heterocycle;
G is a linking moiety spanning 4 to 7 atoms between termini, said linking moiety incorporating at least one of
(a) an sp2 hybridized carbon,
(b) a cyclic structure, and
(c) when the nitrogen bearing $R^8$ and $R^9$ is part of a 4- to 7-membered nitrogenous heterocycle, G may additionally be —$(C_{4-7})$alkylene or —$N(R^{10})$—$(C_{3-6})$alkylene; and
$R^{10}$ is H or $(C_{1-6})$alkyl.

7. A compound chosen from formulae:

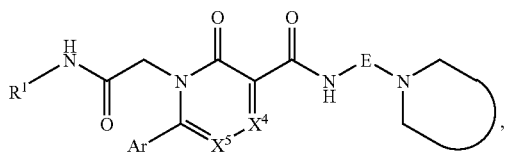

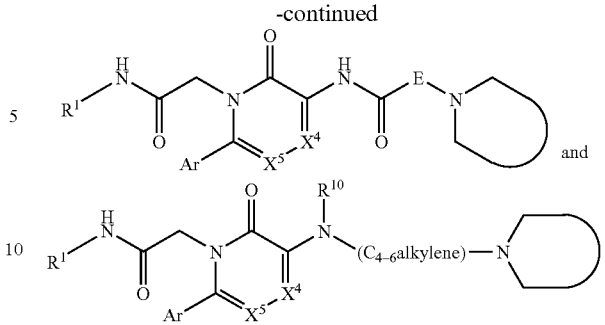

or a pharmaceutically acceptable salt thereof, wherein
$X^4$-$X^5$ is chosen from $CR^4$=$CR^5$;
$R^1$ is chosen from $(C_{1-10})$alkyl, $(C_{3-10})$cycloalkyl, [$(C_{3-10})$cycloalkyl($C_{1-2}$)alkyl], said $(C_{1-10})$alkyl, $(C_{3-10})$cycloalkyl, and [$(C_{3-10})$cycloalkyl($C_{1-2}$)alkyl] being optionally substituted with one or more halogens, $(C_{1-6})$alkoxy, $(C_{2-6})$alkenyl, $(C_{2-6})$alkynyl, phenyl or benzyl;
Ar is $(C_{6-10})$aryl, optionally substituted with 1-3 substituents selected from halogen, hydroxy, cyano, $COOR^5$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens, or Ar is a $(C_{5-10})$heteroaryl optionally substituted with a substituent selected from methyl, $(C_{1-6})$alkyloxy or halogen or $R^2$ is $(C_{4-7})$cycloalkyl;
$R^4$ and $R^5$ are independently chosen from H, $(C_{1-6})$alkyl, $(C_{1-6})$alkyloxy or halogen, said $(C_{1-6})$alkyl, $(C_{1-6})$alkyloxy being optionally substituted with one or more halogens;
$R^{10}$ is H or $(C_{1-6})$alkyl;
E is $(C_{2-10})$hydrocarbon; and

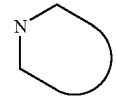

is a saturated nitrogenous heterocycle of 3 to 10 carbons in one or two rings.

8. A compound according to claim 7 or a pharmaceutically acceptable salt thereof, wherein

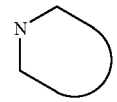

is a piperidine or morpholine ring.

9. A compound of formula:

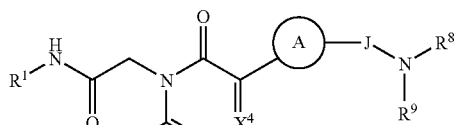

or a pharmaceutically acceptable salt thereof, wherein
X$^4$-X$^5$ is chosen from CR$^4$—CR$^5$;

R$^1$ is chosen from (C$_{1-10}$)alkyl, (C$_{3-10}$)cycloalkyl, [(C$_{3-10}$)cycloalkyl(C$_{1-2}$)alkyl], said (C$_{1-10}$)alkyl, (C$_{3-10}$)cycloalkyl, and [(C$_{3-10}$)cycloalkyl(C$_{1-2}$)alkyl] being optionally substituted with one or more halogens, (C$_{1-6}$)alkoxy, (C$_{2-6}$)alkenyl, (C$_{2-6}$)alkynyl, phenyl or benzyl;

Ar is (C$_{6-10}$)aryl, substituted with 1-3 substituents selected from halogen, hydroxy, cyano, COOR$^5$, phenyl, (C$_{5-6}$)heteroaryl, (C$_{1-6}$)alkyl, (C$_{3-6}$)cycloalkyl, (C$_{1-6}$)alkyloxy and (C$_{3-6}$)cycloalkyloxy, said (C$_{1-6}$)alkyl, (C$_{3-6}$)cycloalkyl, (C$_{1-6}$)alkyloxy and (C$_{3-6}$)cycloalkyloxy being optionally substituted with one or more halogens, or Ar is a (C$_{5-10}$)heteroaryl optionally substituted with a substituent selected from methyl, (C$_{1-6}$)alkyloxy or halogen or R$^2$ is (C$_{4-7}$)cycloalkyl;

R$^4$ and R$^5$ are independently chosen from H, (C$_{1-6}$)alkyl, (C$_{1-6}$)alkyloxy or halogen, said (C$_{1-6}$)alkyl, (C$_{1-6}$)alkyloxy being optionally one or more halogens;

R$^8$ and R$^9$ are hydrogen or alkyl, or NR$^8$R$^9$ is a saturated nitrogenous heterocycle of 3-10 carbons in one or two rings;

J is a direct bond or (C$_{1-6}$)hydrocarbon; and

is a single ring carbocycle or heterocycle of 4 to 7 atoms or a two ring carbocycle or heterocycle of 9 to 13 atoms.

10. A compound according to claim 9 or a pharmaceutically acceptable salt thereof, wherein

is a five or six-membered nitrogenous heterocycle and J is methylene, ethylene or propylene.

11. A compound according to claim 10 or a pharmaceutically acceptable salt thereof, wherein —NR$^8$R$^9$ is chosen from

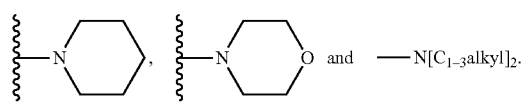

12. A compound according to claim 6 of formula:

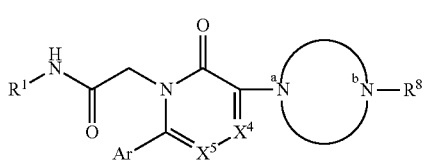

or a pharmaceutically acceptable salt thereof, wherein

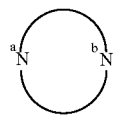

is a nitrogenous single ring heterocycle of 6 to 8 atoms or a two ring heterocycle of 9 to 13 atoms in which the nitrogen labeled b is the nitrogen of claim 1 and the nitrogen labeled a is subsumed in the definition of G in claim 1.

13. A compound according to claim 12 or a pharmaceutically acceptable salt thereof, wherein

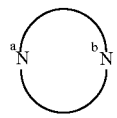

is a hexahydro-1,4-diazepine ring.

14. A compound according to claim 6 chosen from

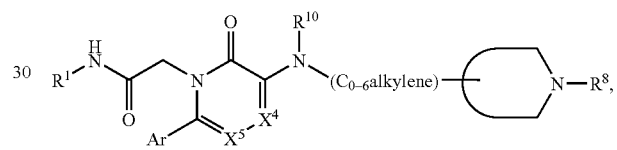

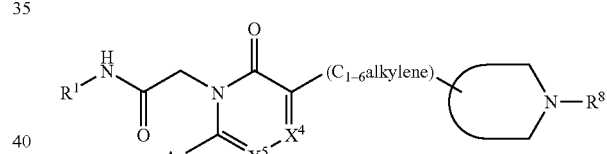

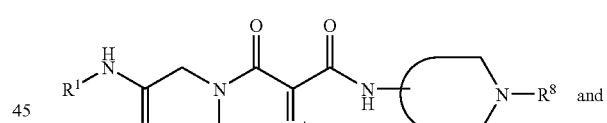

and

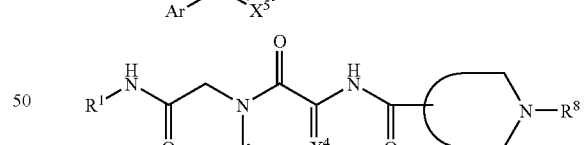

formulae:

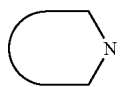

or a pharmaceutically acceptable salt thereof, wherein is a saturated nitrogenous heterocycle of 3 to 10 carbons in one or two rings; and R$^8$ is chosen from hydrogen and C$_{1-10}$ hydrocarbon.

15. A compound according to claim 14 or a pharmaceutically acceptable salt thereof, wherein

is a piperidine ring and $R^8$ is methyl.

16. A compound chosen from formulae:

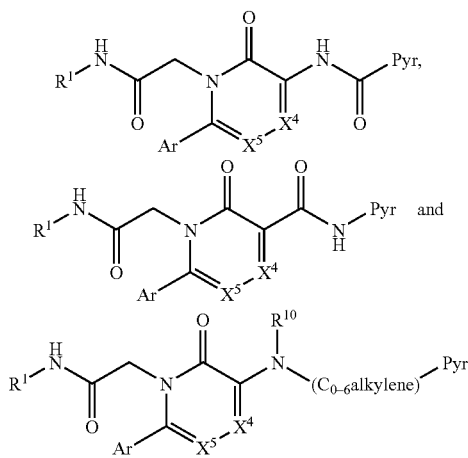

or a pharmaceutically acceptable salt thereof, wherein $X^4$-$X^5$ is $CR^4$—$CR^5$;

$R^1$ is chosen from $(C_{1-10})$alkyl, $(C_{3-6})$cycloalkyl, $(C_{3-6})$cycloalkyl $(C_{1-2})$alkyl, said $(C_{1-10})$alkyl, $(C_{3-6})$cycloalkyl, and $(C_{3-6})$cycloalkyl $(C_{1-2})$alkyl being optionally substituted with one or more halogens, $(C_{2-6})$alkenyl, $(C_{2-6})$alkynyl, phenyl or benzyl;

Ar is $(C_{6-10})$aryl, optionally substituted with 1-3 substituents selected from halogen, hydroxy, cyano, $COOR^5$, phenyl, $(C_{5-6})$heteroaryl, $(C_{1-6})$alkyl, $(C_{3-6})$cycloalkyl, $(C_{1-6})$alkyloxy and $(C_{3-6})$cycloalkyloxy, said $(C_{1-6})$alkyl, $(C_{3-6})$cycloalkyl, $(C_{1-6})$alkyloxy and $(C_{3-6})$cycloalkyloxy being optionally substituted with one or more halogens, or Ar is a $(C_{5-10})$heteroaryl optionally substituted with a substituent selected from methyl, $(C_{1-6})$alkyloxy or halogen or $R^2$ is $(C_{4-7})$cycloalkyl;

$R^4$ and $R^5$ are independently chosen from H, $(C_{1-6})$alkyl, $(C_{1-6})$alkyloxy or halogen, said $(C_{1-6})$alkyl, $(C_{1-6})$alkyloxy being optionally substituted with one or more halogens;

$R^{10}$ is H or $(C_{1-6})$alkyl; and

Pyr is chosen from imidazole and optionally substituted pyridine attached through a carbon.

17. A compound according to claim 1 or a pharmaceutically acceptable salt thereof, wherein $R^1$ is chosen from $C_{3-6}$alkyl, cycloalkyl and $C_{1-3}$alkyl substituted with phenyl, methoxy or alkynyl.

18. A compound according to claim 17 or a pharmaceutically acceptable salt thereof, wherein $R^1$ is chosen from t-butyl, isopropyl, cyclopentyl, α-methylbenzyl, methoxypropyl and propargyl.

19. A compound according to claim 1 or a pharmaceutically acceptable salt thereof, wherein Ar is chosen from phenyl and phenyl substituted with halogen, methyl or methoxy.

20. A pharmaceutical formulation comprising a pharmaceutically acceptable carrier and a compound according to claim 1 or a phamaceutically acceptable salt thereof.

21. A method for treating a disorder chosen from depression, and stress disorders, comprising administering to a patient in need thereof a therapeutically effective amount of a compound according to claim 1 or a pharmaceutically acceptable salt thereof.

* * * * *